(12) United States Patent
Oka

(10) Patent No.: US 6,610,017 B2
(45) Date of Patent: Aug. 26, 2003

(54) CONTINUOUS BLOOD-PRESSURE MONITORING APPARATUS

(75) Inventor: Tohru Oka, Ichinomiya (JP)

(73) Assignee: Colin Corporation, Komaki (JP)

( * ) Notice: Subject to any disclaimer, the term of this patent is extended or adjusted under 35 U.S.C. 154(b) by 66 days.

(21) Appl. No.: 10/028,700

(22) Filed: Dec. 28, 2001

(65) Prior Publication Data

US 2002/0147401 A1 Oct. 10, 2002

(30) Foreign Application Priority Data

Apr. 4, 2001 (JP) ...................................... 2001-105497

(51) Int. Cl.$^7$ ................................................. A61B 5/00
(52) U.S. Cl. ...................................... 600/485; 600/500
(58) Field of Search .............................. 600/485, 490, 600/493–6, 500

(56) References Cited

U.S. PATENT DOCUMENTS

| | | | |
|---|---|---|---|
| 5,139,026 A | | 8/1992 | Niwa |
| 5,762,610 A | * | 6/1998 | Narimatsu et al. .......... 600/500 |
| 5,860,932 A | | 1/1999 | Goto et al. |
| 5,921,936 A | * | 7/1999 | Inukai et al. ................ 600/500 |
| 6,334,849 B1 | * | 1/2002 | Sungawa ..................... 600/485 |
| 6,428,482 B1 | * | 8/2002 | Sungawa et al. ............ 600/485 |
| 6,527,726 B2 | * | 3/2003 | Goto et al. .................. 600/485 |

FOREIGN PATENT DOCUMENTS

| | | |
|---|---|---|
| DE | 198 29 544 C1 | 1/2000 |
| EP | 1 055 394 A2 | 11/2000 |
| EP | 1 095 611 A1 | 5/2001 |
| JP | U 2-82309 | 6/1990 |
| JP | A 7-284479 | 10/1995 |

\* cited by examiner

Primary Examiner—Robert L. Nasser
(74) Attorney, Agent, or Firm—Oliff & Berridge, PLC

(57) ABSTRACT

An apparatus for continuously monitoring a blood pressure of a subject, comprising a cuff; a device for determining a blood pressure of the subject based on a signal obtained while the cuff pressure is changed; a device for determining a relationship between blood pressure and pressure pulse wave, based on a determined blood pressure and a detected magnitude of a first-artery pressure pulse wave; a device for iteratively determining, according to the relationship, a monitor blood pressure based on a magnitude of each pulse of the first-artery pressure pulse wave; a sensor which detects a second-artery pressure pulse wave from a second artery and produces a pressure-pulse-wave signal representing the second-artery pressure pulse wave; a device for extracting, from the pressure-pulse-wave signal, a heart-sound component representing heart sounds; a device for iteratively obtaining a piece of pulse-wave-propagation-velocity-related information, based on a time of occurrence of a periodic point of a pulse of the heart-sound component and a time of occurrence of a periodic point of a corresponding pulse of the second-artery pressure pulse wave; a device for periodically determining a change value of the pieces of information; a device for periodically determining a change value of the monitor blood-pressure values; and a device for comparing the change value of the pieces of information and the change value of the monitor blood-pressure values, with each other, and thereby judging whether the relationship is appropriate.

11 Claims, 17 Drawing Sheets

CONTINUOUS BLOOD-PRESSURE MONITORING APPARATUS

BACKGROUND OF THE INVENTION

1. Field of the Invention

The present invention relates to a continuous blood-pressure monitoring apparatus which includes a pressure-pulse-wave sensor adapted to be pressed against an artery of a living subject via the skin and continuously monitors blood pressure of the subject based on a pressure pulse wave detected by the sensor.

2. Related Art Statement

There is known a continuous blood-pressure monitoring apparatus which includes an inflatable cuff adapted to be worn on a portion of a living subject; a blood-pressure determining means for determining a blood pressure of the subject based on a signal obtained while a pressure in the cuff is slowly changed; a relationship determining means for determining, in advance, a relationship between blood pressure and magnitude of pressure pulse wave, based on the blood pressure determined by the blood-pressure determining means and a magnitude of a pressure pulse wave detected from an artery of the subject; and a blood-pressure monitoring means for successively determining, according to the thus determined relationship, a blood-pressure value of the subject based on each of respective magnitudes of the pressure pulse wave detected from the artery. Since the blood-pressure values successively determined by the continuous blood-pressure monitoring apparatus are very highly reliable, the apparatus can be used in those cases in which strict blood-pressure monitoring is needed. This apparatus is disclosed in, e.g., Japanese Utility Model Document No. 2-82309 or its corresponding U.S. Pat. No. 5,139,026.

In the conventional continuous blood-pressure monitoring apparatus, disclosed in the above-indicated document, a pressure-pulse-wave detecting device for detecting the pressure pulse wave employs a pressure-pulse-wave sensor which is worn on a wrist of a living subject and is pressed against a radial artery of the wrist. In this case, a condition under which the pressure-pulse-wave sensor is pressed against the artery may be changed by, e.g., a change of a state in which the sensor is worn, caused by a physical motion of the subject. Hence, in order to increase the reliability of blood-pressure values determined by the blood-pressure monitoring means, a calibration is periodically carried out to update the relationship between blood pressure and magnitude of pressure pulse wave. In each calibration, the blood-pressure determining means determines a new blood pressure of the subject in a process in which the pressure of the cuff is changed in a prescribed manner, and the relationship determining means determines a new relationship between blood pressure and magnitude of pressure pulse wave, based on the new blood pressure determined by the blood-pressure determining means and a magnitude of the pressure pulse wave detected by the pressure-pulse-wave sensor during the above-indicated process.

However, when each calibration is carried out, the cuff is inflated to press the subject's body, thereby causing the subject to feel discomfort. In addition, the calibration is periodically carried out irrespective of whether the condition under which the sensor is pressed is appropriate or not, and the calibration period needs to be shortened to increase the reliability of continuous monitoring of blood pressure. Thus, the burden exerted on the subject is increased.

In order to solve the above-indicated problem, Japanese Patent Document No. 7-284479 or its corresponding U.S. Pat. No. 5,860,932 discloses a continuous blood-pressure monitoring apparatus in which a pressure-pulse-wave sensor is worn on a portion of a subject that is located on a downstream side of a cuff, a pressure of the cuff is increased at a prescribed rate, and a judging means judges whether a relationship between blood pressure and pressure-pulse-wave magnitude is appropriate, based on a shape or an area of a pressure pulse wave detected by the sensor during the increasing of the cuff pressure. More specifically described, the disclosed apparatus determines, in a state in which the cuff pressure would be substantially equal to, or somewhat higher than, a diastolic blood pressure of the subject, the diastolic blood pressure of the subject by utilizing the fact that the tendency of change of respective shapes or areas of respective heartbeat-synchronous pulses of the pressure pulse wave, successively detected by the sensor during the increasing of the cuff pressure, significantly changes around the diastolic blood pressure, compares the thus determined diastolic blood pressure with a diastolic blood pressure determined based on a magnitude of a heartbeat-synchronous pulse of the pressure pulse wave according to the relationship between blood pressure and pressure-pulse-wave magnitude, and judges whether the relationship is appropriate. If it is judged that the relationship is appropriate, then it is not needed to carry out a calibration, which leads to reducing the discomfort the subject suffers.

However, even in the above-described continuous blood-pressure monitoring apparatus, the cuff pressure is increased up to a value substantially equal to, or somewhat higher than, the diastolic blood pressure, so as to judge whether the relationship is appropriate or not. Thus, the discomfort the subject suffers is not sufficiently reduced.

In addition, in the above-described continuous blood-pressure monitoring apparatus, the pressure-pulse-wave sensor needs to be worn on the subject's portion located on the downstream side of the cuff. On the other hand, in many cases, the continuous blood-pressure monitoring apparatus is used during a surgical operation or in an intensive care unit when or where many devices are connected to the subject and, in some cases, the pressure-pulse-wave sensor cannot be worn on the subject's portion located on the downstream side of the cuff.

SUMMARY OF THE INVENTION

It is therefore an object of the present invention to provide a continuous blood-pressure monitoring apparatus which sufficiently largely reduces discomfort felt by a living subject and sufficiently largely increases freedom of wearing.

The Inventor has carried out extensive studies to achieve the above-indicated object, and has found that pulse-wave-propagation-velocity-related information, such as a pulse-wave propagation time or a pulse-wave propagation velocity, that is related to a velocity at which a pulse wave propagates in a living subject, is not so accurate as a monitor blood pressure determined by a blood-pressure monitoring means based on a pressure pulse wave detected by a pressure-pulse-wave detecting probe from the subject, but it does change in relation with a change of the blood pressure of the subject, and that if the comparison between a change of the monitor blood pressure and a change of the pulse-wave-propagation-velocity-related information obtained concurrently with the monitor blood pressure shows that the difference between the two changes is not so great, it can be judged that a pressure-pulse-wave sensor of the pressure-pulse-wave detecting device is appropriately pressed. In addition, if a pressure pulse wave is detected from a portion of the subject that is distant from the chest of the subject, the detected pressure pulse wave contains a heart-sound component. That is, since the single sensor can detect the two heartbeat-synchronous signals, i.e., the heart sounds and the pulse wave, the pulse-wave-propagation-velocity-related information can be obtained by using the single sensor worn on the subject.

Moreover, the Inventor has found that if the heart-sound component is extracted from the pressure pulse wave detected to determine the monitor blood pressure, and the pulse-wave-propagation-velocity-related information is obtained based on the pressure pulse wave detected to determine the monitor blood pressure, and the heart-sound component extracted from the pressure pulse wave, it is not needed to wear, on the subject, another sensor to obtain the pulse-wave-propagation-velocity-related information. That is, the sensor to obtain the pulse-wave-propagation-velocity-related information may be the same as, or different from, the pressure-pulse-wave sensor to detect the pressure pulse wave used to determine the monitor blood pressure. The present invention has been developed based on these findings.

The above object has been achieved by the present invention. According to a first aspect of the present invention, there is provided an apparatus for continuously monitoring a blood pressure of a living subject, comprising an inflatable cuff which is adapted to be wound around a portion of the subject; a blood-pressure determining means for determining a blood pressure of the subject based on a signal obtained while a pressure in the cuff is changed; a relationship determining means for determining a relationship between blood pressure and magnitude of pressure pulse wave, based on the blood pressure determined by the blood-pressure determining means and a magnitude of a first-artery pressure pulse wave detected from a first artery of the subject; a blood-pressure monitoring means for iteratively determining, according to the thus determined relationship, a monitor blood-pressure value of the subject based on a magnitude of each of a plurality of heartbeat-synchronous pulses of the first-artery pressure pulse wave detected from the first artery; a first pressure-pulse-wave sensor which is adapted to be worn on a portion of the subject that is distant from a chest of the subject, detects a second-artery pressure pulse wave that is produced by a second artery of the portion, and produces a pressure-pulse-wave signal representing the detected second-artery pressure pulse wave; a heart-sound extracting means for extracting, from the pressure-pulse-wave signal produced by the pressure-pulse-wave sensor, a heart-sound component representing heart sounds generated by a heart of the subject; a pulse-wave-propagation-velocity-related-information obtaining means for iteratively obtaining a piece of pulse-wave-propagation-velocity-related information which is related to a velocity at which the second-artery pressure pulse wave propagates through the second artery of the subject, based on a time of occurrence of a prescribed periodic point of a heartbeat-synchronous pulse of the heart-sound component extracted by the heart-sound extracting means and a time of occurrence of a prescribed periodic point of a corresponding heartbeat-synchronous pulse of the second-artery pressure pulse wave detected by the pressure-pulse-wave sensor; a propagation-velocity-related-information-change-value determining means for periodically determining, at a prescribed judgment period, a change value of the pieces of pulse-wave-propagation-velocity-related information obtained by the pulse-wave-propagation-velocity-related-information obtaining means; a monitor-blood-pressure-change-value determining means for periodically determining, at the judgment period, a change value of the monitor blood-pressure values determined by the blood-pressure monitoring means; and a relationship checking means for comparing the change value of the pieces of pulse-wave-propagation-velocity-related information, determined by the propagation-velocity-related-information-change-value determining means, and the change value of the monitor blood-pressure values, determined by the monitor-blood-pressure-change-value determining means, with each other, and thereby judging whether the relationship between blood pressure and magnitude of pressure pulse wave, determined by the relationship determining means, is appropriate. The first and second arteries may be the same as, or different from, each other, and the first-artery and second-artery pressure pulse waves may be the same as, or different from, each other.

According to this feature, the heart-sound extracting means extracts the heart-sound component from the pressure pulse wave detected by the first pressure-pulse-wave sensor; the pulse-wave-propagation-velocity-related-information obtaining means obtains the pulse-wave-propagation-velocity-related information based on the heart-sound component and the pressure pulse wave detected by the first pressure-pulse-wave sensor; and the propagation-velocity-related-information-change-value determining means determines, at the prescribed judgment period, the change value of the pulse-wave-propagation-velocity-related information. Since the pulse-wave-propagation-velocity-related information changes with the change of blood pressure of the subject, the change value of the pulse-wave-propagation-velocity-related information also changes with the change of blood pressure. In addition, the change value of the monitor blood-pressure value determined by the monitor-blood-pressure-change-value determining means also changes with the change of blood pressure. In the case where the condition under which a pressure-pulse-wave detecting device is worn on the subject has changed and the monitor blood-pressure value determined by the blood-pressure monitoring means is not accurate, the change value of the monitor blood-pressure value largely differs from the change value of the pulse-wave-propagation-velocity-related information. Therefore, the relationship checking means compares the change value of the monitor blood-pressure value and the change value of the pulse-wave-propagation-velocity-related information, with each other, and judges whether the relationship between blood pressure and pressure pulse wave, determined by the relationship determining means, is appropriate. Therefore, a longer period can be employed at which the blood-pressure determining means is operated to update the relationship between blood pressure and pressure pulse wave, and accordingly the discomfort the subject feels can be reduced. Moreover, since the pulse-wave-propagation-velocity-related information can be obtained by using only the first pressure-pulse-wave sensor worn on the subject, and it is not needed to wear the first pressure-pulse-wave sensor on the downstream side of the cuff, the first pressure-pulse-wave sensor enjoys an increased freedom of wearing.

According to a second aspect of the present invention, there is provided an apparatus for continuously monitoring a blood pressure of a living subject, comprising an inflatable cuff which is adapted to be wound around a portion of the subject; a blood-pressure determining means for determining a blood pressure of the subject based on a signal obtained while a pressure in the cuff is changed; a first relationship determining means for determining a relationship between blood pressure and magnitude of pressure pulse wave, based on the blood pressure determined by the blood-pressure determining means and a magnitude of a first-artery pressure pulse wave detected from a first artery of the subject; a blood-pressure monitoring means for iteratively determining, according to the thus determined relationship, a monitor blood-pressure value of the subject based on a magnitude of each of a plurality of heartbeat-synchronous pulses of the first-artery pressure pulse wave detected from the first artery; a first pressure-pulse-wave sensor which is adapted to be worn on a portion of the subject that is distant from a chest of the subject, detects a second-artery pressure pulse wave that is produced by a second artery of the portion, and produces a pressure-pulse-wave signal representing the detected second-artery pressure pulse wave; a heart-sound extracting means for extracting, from the pressure-pulse-wave signal produced by the pressure-pulse-wave sensor, a heart-sound component representing heart sounds generated by a heart of the subject; a standard-pulse-wave-propagation-velocity-related-information obtaining means for obtaining, as a standard piece of pulse-wave-propagation-velocity-related information, a piece of pulse-wave-propagation-velocity-related information which is related to a velocity at which the second-artery pressure pulse wave propagates through the second artery of the subject, based on a time of occurrence of a prescribed periodic point of a heartbeat-synchronous pulse of the heart-sound component in a first time duration comprising at least one of a first time period in which the pressure of the cuff is changed, a prescribed preceding time period preceding the first time period, and a prescribed following time period following the first time period, and a time of occurrence of a prescribed periodic point of a corresponding heartbeat-synchronous pulse of the second-artery pressure pulse wave in the first time duration; a second relationship determining means for determining a second relationship between blood pressure and pulse-wave-propagation-velocity-related information, based on the blood pressure determined by the blood-pressure determining means and the standard piece of pulse-wave-propagation-velocity-related information obtained by the standard-pulse-wave-propagation-velocity-related-information obtaining means; a judgment-pulse-wave-propagation-velocity-related-information obtaining means for obtaining, as a judgment piece of pulse-wave-propagation-velocity-related information, a piece of pulse-wave-propagation-velocity-related information which is related to the velocity at which the second-artery pulse wave propagates through the second artery of the subject, based on a time of occurrence of a prescribed periodic point of a heartbeat-synchronous pulse of the heart-sound component extracted by the heart-sound extracting means, and a time of occurrence of a prescribed periodic point of a corresponding heartbeat-synchronous pulse of the second-artery pressure pulse wave detected by the pressure-pulse-wave sensor, at a prescribed judgment period; an estimated-blood-pressure determining means for determining, according to the second relationship, an estimated blood-pressure value of the subject based on the judgment piece of pulse-wave-propagation-velocity-related information obtained by the judgment-pulse-wave-propagation-velocity-related-information obtaining means; and a relationship checking means for comparing, at the judgment period, the estimated blood-pressure value determined by the estimated-blood-pressure determining means, and a monitor blood-pressure value determined by the blood-pressure monitoring means based on a magnitude of a heartbeat-synchronous pulse of the first-artery pressure pulse wave detected at a time around a time when the judgment piece of pulse-wave-propagation-velocity-related information is obtained by the judgment-pulse-wave-propagation-velocity-related-information obtaining means, with each other, and thereby judging whether the relationship between blood pressure and magnitude of pressure pulse wave, determined by the first relationship determining means, is appropriate.

According to this feature, the estimated-blood-pressure determining means determines the estimated blood-pressure value based on the second pulse-wave-propagation velocity-related information, according to the relationship between blood pressure and pulse-wave-propagation-velocity-related information. If the condition under which a pressure-pulse-wave detecting device is worn on the subject has changed and accordingly the monitor blood-pressure value determined by the blood-pressure monitoring means is not accurate, the monitor blood-pressure value largely differs from the estimated blood-pressure value. Hence, the relationship checking means compares the estimated blood-pressure value and the monitor blood-pressure value determined by the blood-pressure monitoring means, with each other, and judges whether the relationship between blood pressure and pressure pulse wave, determined by the first relationship determining means, is appropriate or not. Therefore, a longer period can be employed at which the blood-pressure determining means is operated to update the relationship between blood pressure and pressure pulse wave, and accordingly the discomfort the subject feels can be reduced. Moreover, since the standard pulse-wave-propagation-velocity-related information or the judgment pulse-wave-propagation-velocity-related information can be obtained by using only the first pressure-pulse-wave sensor worn on the subject, and it is not needed to wear the first pressure-pulse-wave sensor on the downstream side of the cuff, the first pressure-pulse-wave sensor enjoys an increased freedom of wearing.

According to a preferred feature of the present invention, the apparatus further comprises a second pressure-pulse-wave sensor which is adapted to be pressed against the first artery of the subject and detects the first-artery pressure pulse wave generated by the first artery, and the first pressure-pulse-wave sensor is adapted to be worn on the portion of the subject that is more proximal to the heart of the subject than the first artery against which the second pressure-pulse-wave sensor is adapted to be pressed.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
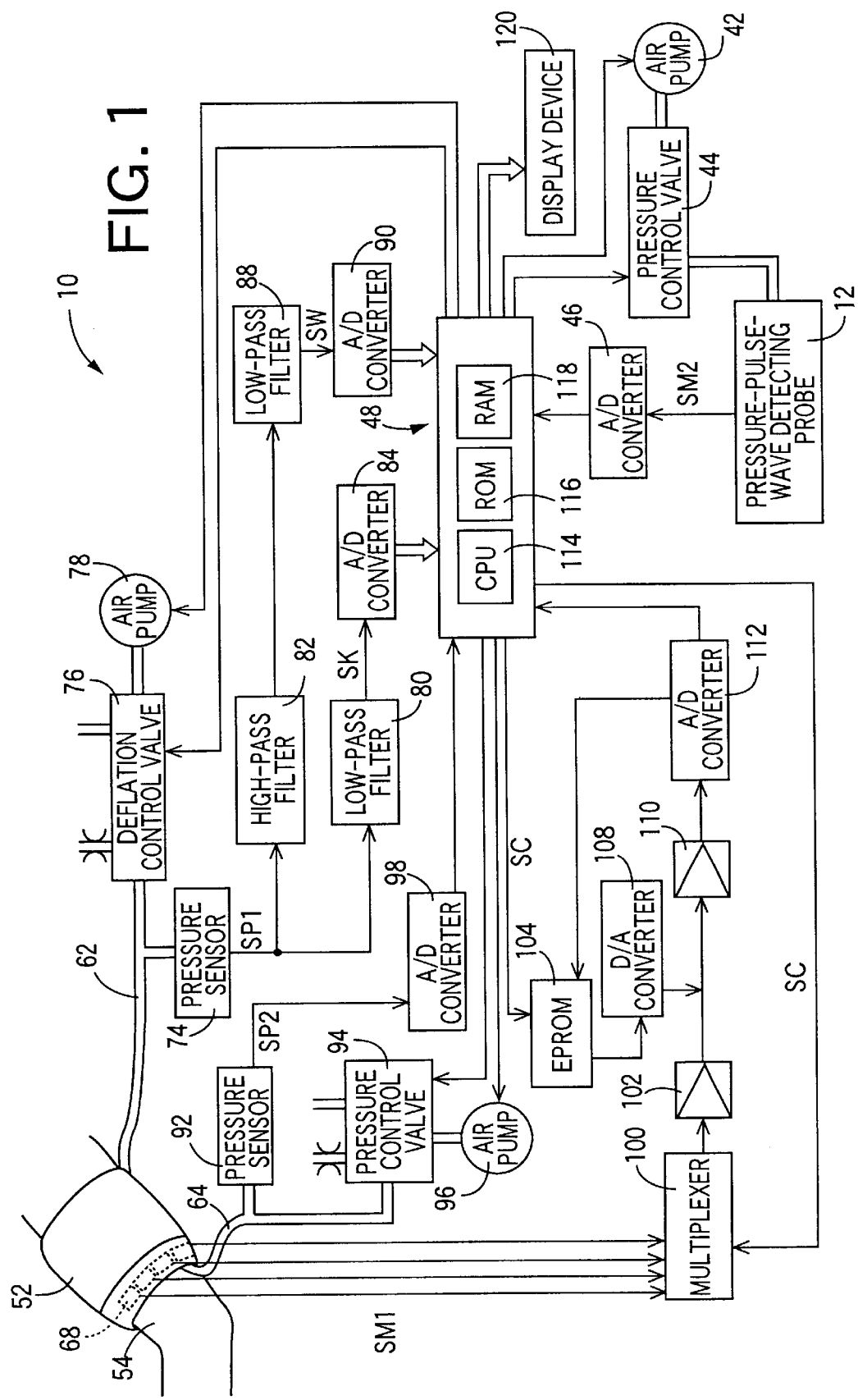
FIG. 1 is a diagrammatic view showing a construction of a continuous blood-pressure monitoring apparatus to which the present invention is applied.

Hereinafter, there will be described a preferred embodiment of the present invention in detail by reference to the drawings. FIG. 1 is a diagrammatic view showing a construction of a continuous blood-pressure monitoring apparatus 10 to which the present invention is applied; and FIG. 2 is a partly-cut-away view of a pressure-pulse-wave detecting probe 12 functioning as a pressure-pulse-wave detecting device.

Figure 2:
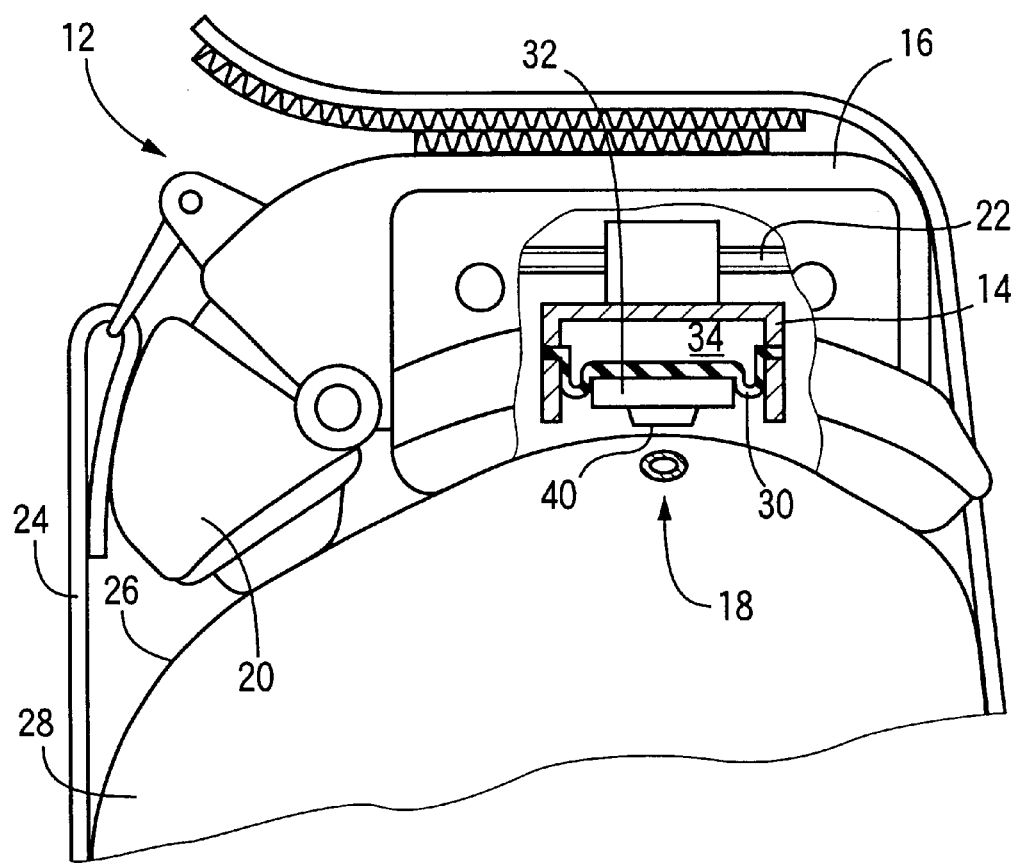
FIG. 2 is a view of a pressure-pulse-wave detecting probe of the apparatus of FIG. 1, a portion of the probe being cut away.

First, the construction of the pressure-pulse-wave detecting probe 12 shown in FIG. 2 is described below. The pressure-pulse-wave detecting probe 12 includes a case 16 which accommodates a container-like sensor housing 14; and a feed screw 22 which is threadedly engaged with the sensor housing 14 and is rotated by an electric motor, not shown, provided in a drive section 20 of the case 16 so as to move the sensor housing 14 in a widthwise direction of a radial artery 18. With the help of a fastening band 24 which is connected to the case 16, the case 16 is detachably attached to a wrist 28 of a patient as a living subject, such that an open end of the sensor housing 14 is opposed to a body surface 26 of the wrist. In addition, the probe 12 includes a second pressure-pulse-wave sensor 32 (a first pressure-pulse-wave sensor 68 will be described later) which is secured via a diaphragm 30 to an inner wall of the sensor housing 14, such that the second sensor 32 is movable relative to the housing 14 and is advanceable out of the open end of the same 14. The sensor housing 14, the diaphragm 30, etc. cooperate with one another to define a pressure chamber 34.

The sensor housing 14 and the diaphragm 30 cooperate with each other to provide a pressing device 36 which presses the second pressure-pulse-wave sensor 32 against the radial artery 18, with an optimum pressing force $P_{HDPO}$, described later. The feed screw 22 and the not-shown motor cooperate with each other to provide a pressing-position changing device or a widthwise-direction moving device 38 which moves the second pressure-pulse-wave sensor 32 in the widthwise direction of the radial artery 18 and thereby changes a pressing position where the second sensor 32 is pressed.

The second pressure-pulse-wave sensor 32 includes a semiconductor chip provided by, e.g., a monocrystalline silicon, and having a press surface 40, and a number of semiconductor pressure-sensing elements (not shown) arranged on the press surface 40 at a regular interval of about 0.2 mm in the widthwise direction of the radial artery 1856 (i.e., the direction of movement of the second sensor 32 parallel to the feed screw 22). The second sensor 32 is pressed against the body surface 26 of the wrist 28 right above the radial artery 18, to detect a radial-artery pressure pulse wave PW(t), i.e., an oscillatory pressure wave which is produced from the radial artery 18 and is propagated to the body surface 28, and outputs a second pressure-pulse-wave signal $SM_2$ (a first pressure-pulse-wave signal $SM_2$ will be described later) representing the radial-artery pressure pulse wave PW(t).

Next, FIG. 1 will be described. The pressure chamber 34 of the pressure-pulse-wave detecting probe 12 is supplied with a pressurized air from an air pump 42 via a pressure-control valve 44 so that the second pressure-pulse-wave sensor 32 is pressed against the body surface 26 with a pressing force $P_{HDP}$ corresponding to the pressure in the pressure chamber 34. In addition, the second sensor 32 supplies the second pressure-pulse-wave signal $SM_2$ to a control device 48 via an A/D (analog-to-digital) converter 46.

Figure 3:
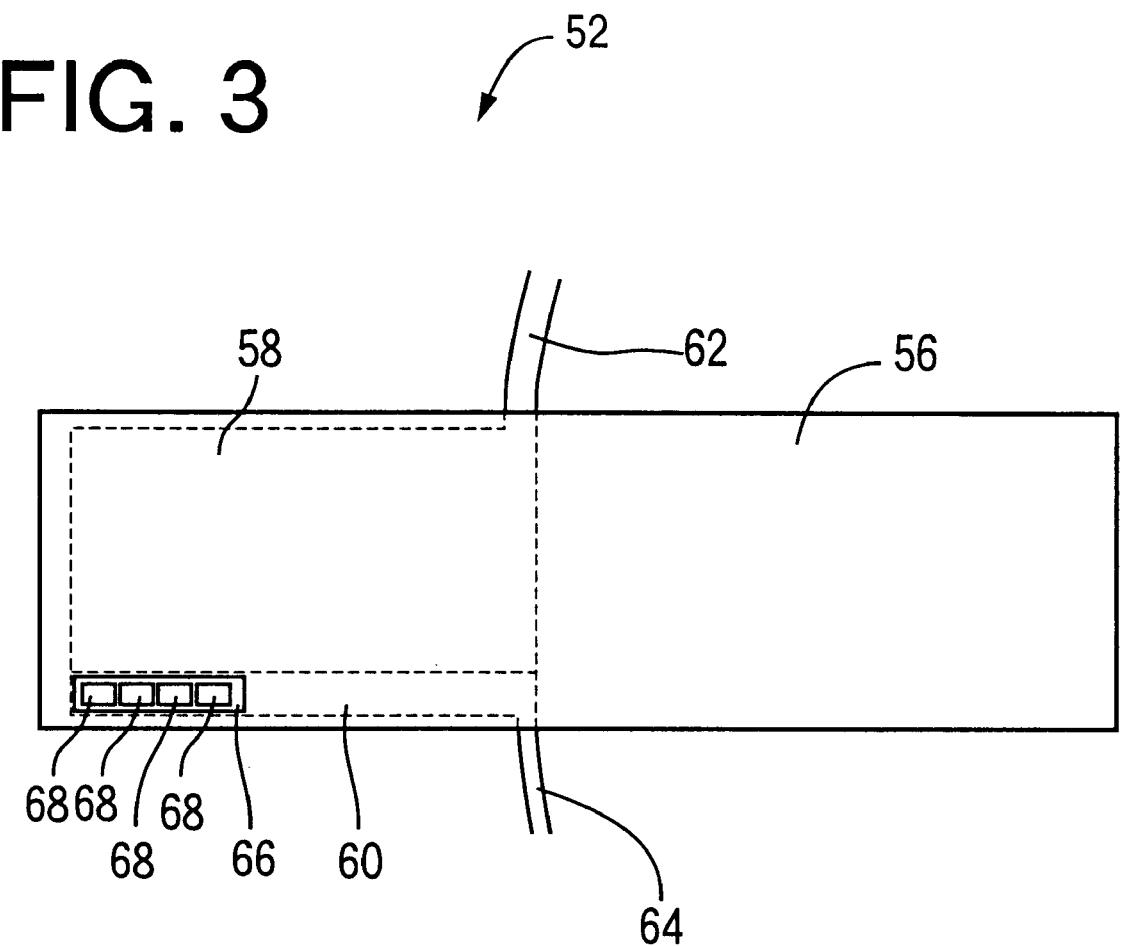
FIG. 3 is a development view of an inflatable cuff of the apparatus of FIG. 1.

In FIG. 1, reference numeral 52 designates an inflatable cuff which is wound around an upper arm 54 of the patient. The upper arm 54 around which the cuff 52 is wound may be either the same arm as that on which the pressure-pulse-wave detecting probe 12 is worn, or the other arm than the arm on which the probe 12 is worn. FIG. 3 is a development view of the cuff 52. As shown in FIG. 3, the cuff 52 includes a belt-like cover bag 56 which is formed of a non-stretchable and considerably rigid cloth and has substantially the same length as that of a common inflatable cuff which is used to measure a blood pressure of an upper arm of a patient. However, a width of the cuff 52 is longer than that of the common cuff by a length corresponding to a width of a small cuff 60, described below.

In the cover bag 56, there are provided a large cuff 58 and the small cuff 60 each of which has substantially the same length (e.g., 24 cm) as that of a circumferential length of the upper arm 54 and is formed of rubber. The large cuff 58 has substantially the same width as that of a rubber bag employed in the common cuff. The width of the small cuff 60 is smaller than that of the large cuff 58 and is, for example, 2 cm. The large cuff 58 and the small cuff 60 are provided such that respective one long sides thereof are adjacent to each other. In a state in which the cuff 52 is wound around the upper arm 54, the small cuff 60 is positioned at a distal-side end of the cuff 52. The large cuff 58 and the small cuff 60 are connected to respective pipings 62, 64 for supplying pressurized air thereto.

A flexible support plate 66 which has substantially the same width as that of the small cuff 60 is fixed to an inner surface of the cuff 52 that contacts the upper arm 54 when the cuff 52 is wound around the same 54. More specifically described, the support plate 66 is fixed to a portion of the inner surface of the cuff 52 that corresponds to the small cuff 60, so that when the cuff 52 is wound around the upper arm 54, the support plate 66 is pressed by the small cuff 60. The support plate 66 supports four first pressure-pulse-wave sensors 68 such that the four first sensors 68 are arranged along a straight line in a lengthwise direction of the plate 66. Between each pair of adjacent sensors 68, there is provided a considerably small space of 0.9 mm length.

Figure 4:
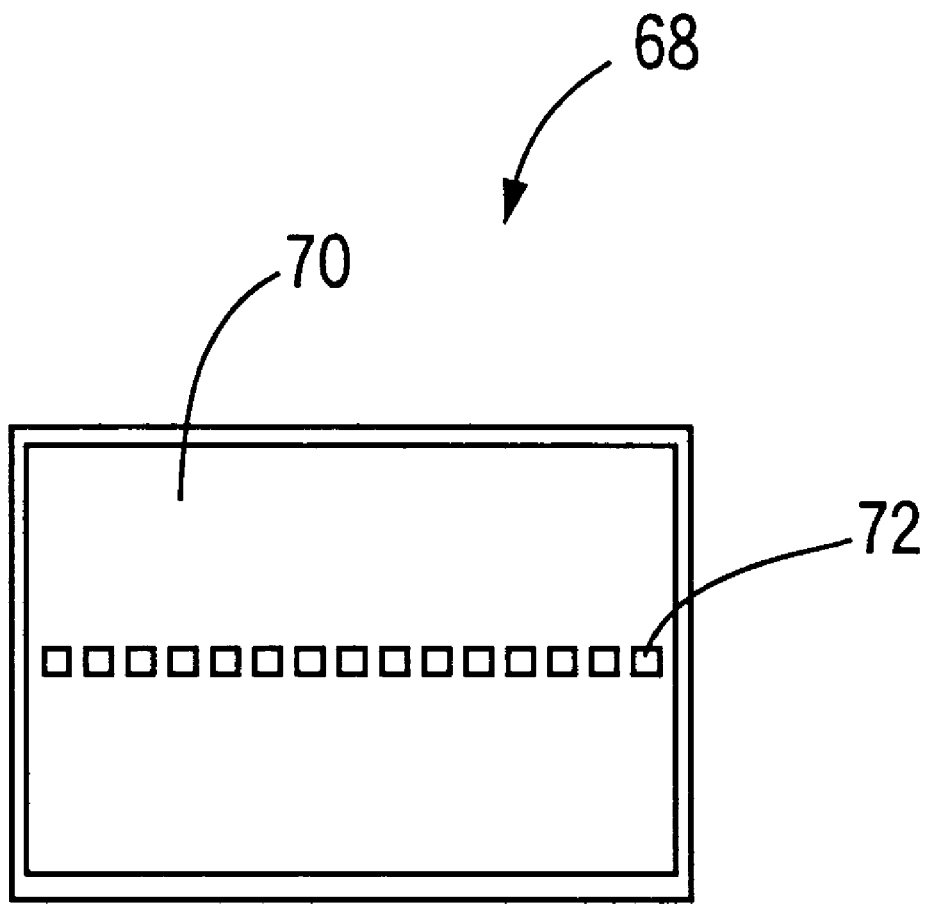
FIG. 4 is a plan view of a first pressure-pulse-wave sensor of the apparatus of FIG. 1.

FIG. 4 is a plan view of one of the four first pressure-pulse-wave sensors 68. The first sensor 68 has a press surface 70 which is defined by a semiconductor chip such as monocrystalline silicon and has a length of about 13 mm in a lengthwise direction of the cuff 52 (i.e., in a left-right direction in FIG. 4). In the press surface 70, there are provided a number of semiconductor pressure-sensing elements (or pressure-detecting elements) 72 at a regular interval of distance along a straight line in the lengthwise direction of the cuff 52. In the present embodiment, each first pressure-pulse-wave sensor 68 has fifteen pressure sensing elements 72 which are arranged at a regular spacing interval of 0.2 mm.

Back to FIG. 1, the large cuff 58 is connected to a pressure sensor 74, a deflation control valve 76, and an air pump 78 via the piping 62. The deflation control valve 76 is selectively placed in a pressure-supply position in which the control valve 76 permits a pressurized air to be supplied from the air pump 78 to the large cuff 58, a slow-deflation position in which the control valve 76 permits the pressurized air to be slowly discharged from the large cuff 58, and a quick-deflation position in which the control valve 76 permits the pressurized air to be quickly discharged from the large cuff 58.

The pressure sensor 74 detects an air pressure $P_{K1}$ in the large cuff 58, and supplies a first pressure signal SP1 representing the detected pressure $P_{K1}$, to each of a low-pass filter 80 and a high-pass filter 82 via an amplifier, not shown. The low-pass filter 80 extracts, from the pressure signal SP1, a static-pressure component contained in the signal SP1, i.e., a cuff-pressure signal SK representing the pressing pressure of the large cuff 58. The cuff-pressure signal SK is supplied to the control device 48 via an A/D converter 84. The high-pass filter 82 extracts, from the pressure signal SP1, an alternating component having frequencies not lower than 0.8 Hz, and supplies the thus extracted alternating-component signal to a low-pass filter 88 via an amplifier, not shown. The low-pass filter 88 extracts, from the alternating-component signal supplied from the high-pass filter 42, an alternating component having frequencies not higher than 10.8 Hz. This alternating-component signal provides a cuff-pulse-wave signal SW representing the alternating component of the pressure signal SP1. The cuff-pulse-wave signal SW is supplied to the control device 48 via an A/D converter 90.

The small cuff 60 is connected to a pressure sensor 92, a pressure control valve 94, and an air pump 96 via the piping 64. The pressure sensor 92 detects an air pressure $P_{K2}$ in the small cuff 60, and supplies a second pressure signal SP2 representing the detected pressure $P_{K2}$, to the control device 48 via an A/D converter 98. The pressure control valve 94 changes the pressure of the pressurized air supplied from the air pump 96, and supplies the pressurized air having the thus changed pressure to the small cuff 60.

A multiplexer 100 sequentially supplies, according to switch signals SC supplied from the control device 48, the respective first pressure-pulse-wave signals SM1 supplied from the sixty pressure-sensing elements 72 of the four first pressure-pulse-wave sensors 68, each signal SM1 for a prescribed time duration, to an amplifier 102. Each of the first pressure-pulse-wave signals SM1 represents a brachial-artery pressure pulse wave. An EPROM (erasable programmable ROM) 104 stores, for the sixty pressure-sensing elements 72, respective correction signals for eliminating respective individual sensitivity differences among the pressure-sensing elements 72, and sequentially supplies, according to the switch signals SC supplied from the control device 48, i.e., in synchronism with the respective switching operations of the multiplexer 100, the respective correction signals, to a D/A (digital-to-analog) converter 108, in such a manner that the respective correction signals sequentially correspond to the respective pressure-sensing elements 72 supplying the respective first pressure-pulse-wave signals SM1 being currently dealt with by the multiplexer 100.

Each of the sixty first pressure-pulse-wave signals SM1 that have been amplified by the amplifier 102, and a corresponding one of the sixty correction signals that have been converted to respective analog signals by the D/A converter 108 are supplied to an amplifier 110. Thus, the sixty corrected first pressure-pulse-wave signals SM1 supplied to the amplifier 110 have a uniform sensitivity. Each of the sixty corrected first pressure-pulse-wave signals SM1 is supplied to an I/O (input-and-output) port of the control device 48 via an A/D converter 112.

The control device 48 is provided by a so-called microcomputer including a CPU (central processing unit) 114, a ROM (read only memory) 116, and a RAM random access memory) 118. The CPU 114 processes signals according to the control programs pre-stored in the ROM 116 by utilizing the temporary-storage function of the RAM 118, and controls the deflation control valve 76 and the air pump 78 to carry out a blood-measure measuring operation, changes the pressing force $P_{HDP}$ applied to the second pressure-pulse-wave sensor 32, successively determines monitor blood-pressure values MBP of the patient, and controls a display device 120 to display the thus determined monitor blood-pressure values MBP.

Figure 5:
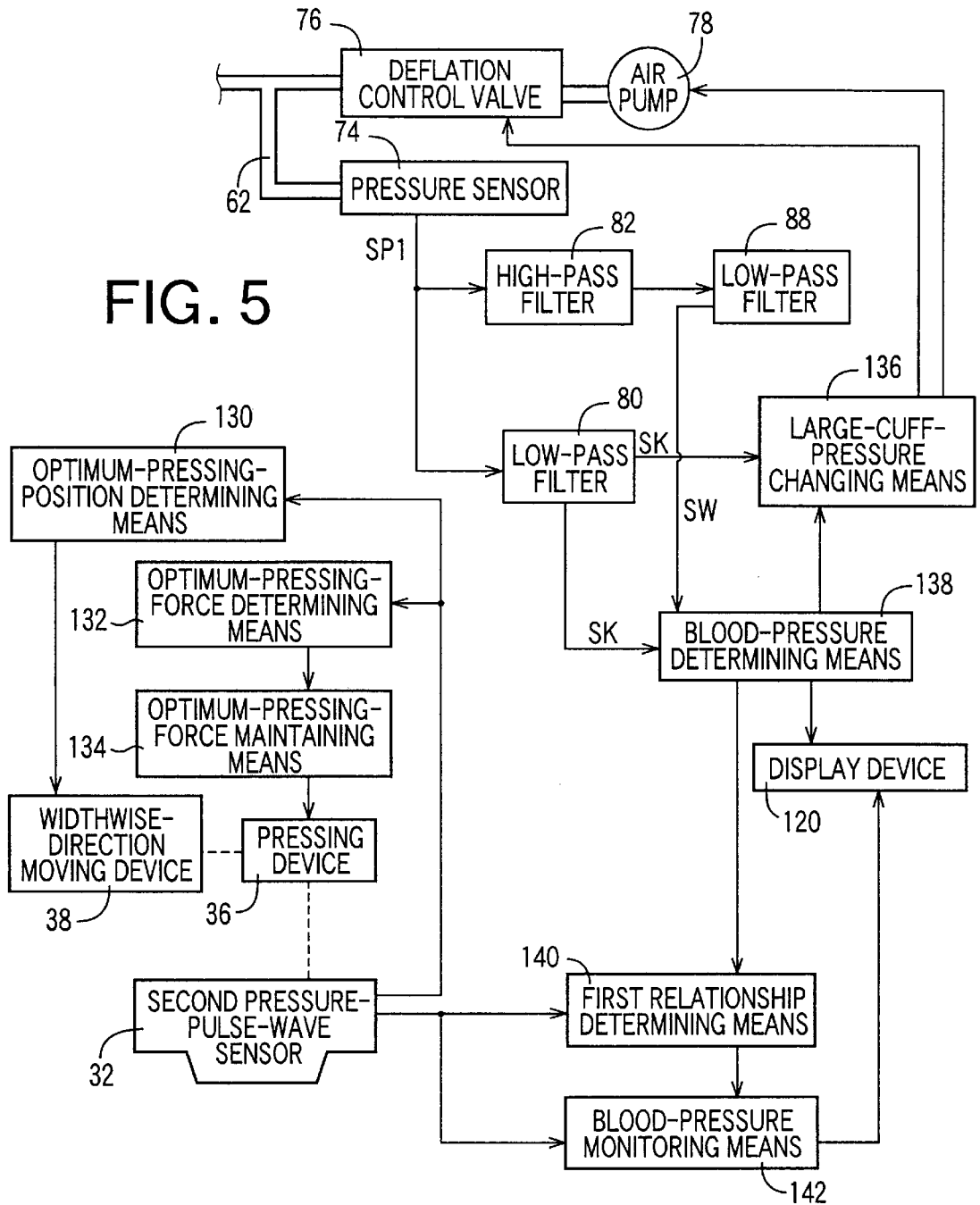
FIG. 5 is a block diagram for explaining essential control functions of a control device of the apparatus of FIG. 1 that relate to the function of successively determining monitor blood-pressure values MBP.

FIG. 5 is a block diagram for explaining essential functions of the control device 48 that relate to the function of successively determining monitor blood-pressure values MBP.

An optimum-pressing-position determining means 130 operates when a prescribed pressing-position changing condition (i.e., an APS-starting condition) is satisfied, for example, when the pressure-pulse-wave detecting probe 12 is initially worn on the patient, or when the second pressure-pulse-wave sensor 32 is largely moved relative to the radial artery 18 so that one of the pressure-sensing elements of the second sensor 32 that detects the greatest one of the respective amplitudes of heartbeat-synchronous pulses detected by all the pressure-sensing elements is located in one of prescribed opposite end portions of the array of pressure-sensing elements provided in the press surface 40. When the APS-starting condition is satisfied, first, the determining means 130 operates the pressing device 36 to press the second pressure-pulse-wave sensor 32 at a first prescribed pressing pressure $P_1$ which would be sufficiently lower than an optimum pressing pressure $P_{HDPO}$ and, in this state, judges whether the one pressure-sensing element that detects the greatest amplitude is located in a prescribed middle range of the array of pressure-sensing elements. If a negative judgment is made, that is, if the one pressure-sensing element that detects the greatest amplitude is not positioned in the prescribed middle range, then the determining means 130 operates the pressing device 36 to move the second sensor 32 away from the body surface 26 and operates the moving device 38, and again performs the above-described pressing and judging operations. Meanwhile, if a positive judgment is made indicating that the second sensor 32 has been positioned at an optimum pressing position, the determining means 130 determines the pressure-sensing element detecting the greatest amplitude, as a middle pressure-sensing element (i.e., an active element), and stores data indicating the pressure-sensing element determined as the active element. Then, the determining means 130 allows an optimum-pressing-force determining means 132 to operate.

Figure 6:
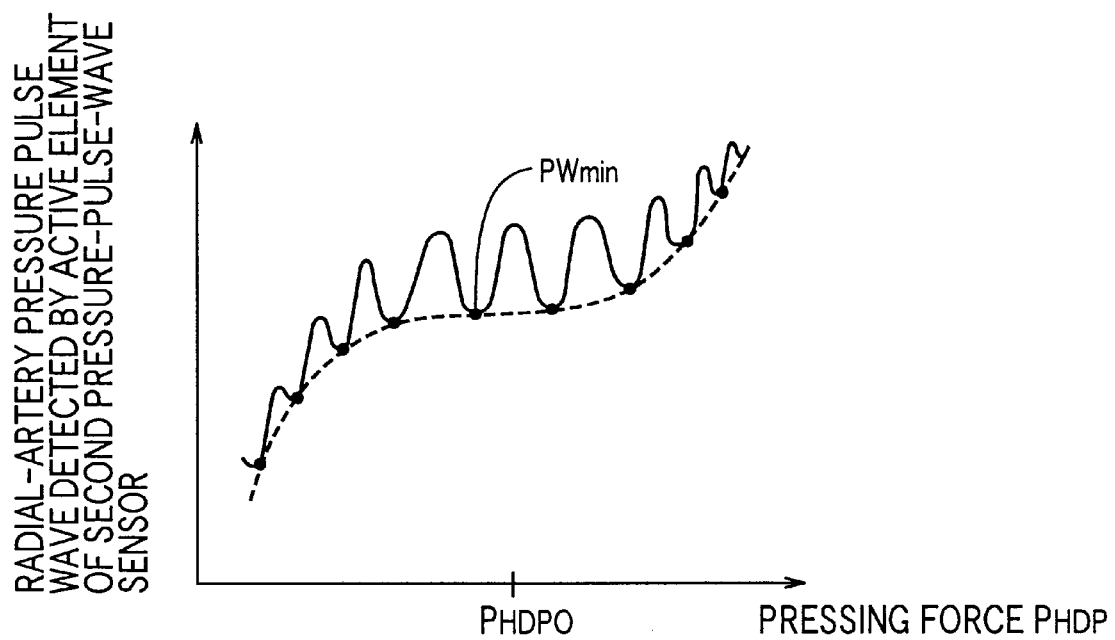
FIG. 6 is a graph for explaining a manner in which an optimum pressing force is determined by an optimum-pressing-force determining means shown in FIG. 5.

The optimum-pressing-force determining means 132 continuously changes the pressing pressure $P_{HDP}$ applied to the second pressure-pulse-wave sensor 32 positioned at the optimum pressing position by the optimum-pressing-position determining means 130, and determines an optimum pressing pressure $P_{DHPO}$ based on the radial-artery pressure pulse wave PW detected by the active element of the second sensor 32. The optimum pressing pressure $P_{DHPO}$ may be determined as follows: First, as shown in a two-dimensional graph shown in FIG. 6, respective minimal values $PW_{min}$ of respective heartbeat-synchronous pulses of the radial-artery pressure pulse wave PW detected by the active element of the second sensor 32 when the pressing pressure $P_{HDP}$ is continuously increased in a pressure range which would include the optimum pressing pressure $P_{DHPO}$, are determined, and then a curve (indicated at broken line in FIG. 6) connecting the respective minimal values $PW_{min}$ of the radial-artery pressure pulse wave PW is determined. Further, the optimum pressing pressure $P_{DHPO}$ is determined as a pressure which falls within a pressure range which has a prescribed width and whose middle pressure is equal to a middle pressure of a pressure range in which the thus determined curve is substantially horizontal. If the radial artery 18 is pressed by the second sensor 32 with the pressure falling within the latter pressure range, a portion of the wall of the radial artery 18 that is pressed by the second sensor 32 is so deformed as to be substantially flat.

An optimum-pressing-force maintaining means 134 operates the air pump 42 and the pressure control valve 44 to maintain the pressing pressure $P_{HDP}$ applied by the pressing device 36 to the second pressure-pulse-wave sensor 32, at the optimum pressing pressure $P_{HDPO}$ determined by the optimum-pressing-force determining means 132.

A large-cuff-pressure changing means 136 controls the deflation control valve 76 and the air pump 78 to quickly increase the pressing pressure of the large cuff 58 up to a prescribed target pressure PM1, e.g., 180 mmHg and then slowly decrease the pressing pressure at a rate of from 2 to 5 mmHg/sec. After a blood-pressure determining means 138, described below, determines a blood pressure BP of the patient, the large-cuff-pressure control means 136 quickly decreases the pressing pressure.

The blood-pressure determining means 138 determines, based on the change of the cuff-pulse-wave signal SW obtained during the slow decreasing of the pressing pressure of the large cuff 58 by the large-cuff-pressure changing means 136, a systolic blood pressure $BP_{SYS}$, a mean blood pressure $BP_{MEAN}$, and a diastolic blood pressure $BP_{DIA}$ of the patient, according to well-known oscillometric method, and controls the display device 120 to display the thus determined blood pressure values $BP_{SYS}$, etc.

Figure 7:
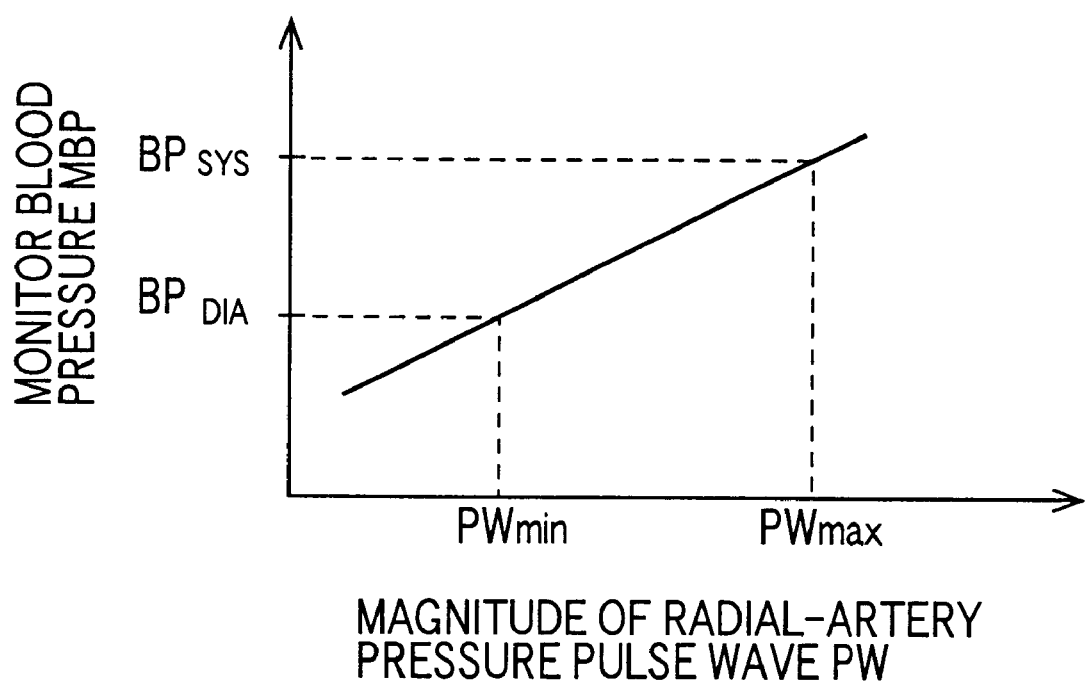
FIG. 7 is a graph showing an example of a relationship determined by a first relationship determining means shown in FIG. 5.

A first relationship determining means 140 operates, at a prescribed calibration period Tc of from 10 to 30 minutes, the blood-pressure determining means 138 determines, in advance, a relationship between blood pressure and magnitude of pressure pulse wave, based on the blood-pressure values BP determined by the blood-pressure determining means 138 and magnitudes of the radial-artery pressure pulse wave PW detected by the active element of the second pressure-pulse-wave sensor 32 at any time in a prescribed time duration consisting of a blood-pressure-measurement period in which the blood-pressure values BP are determined by the blood-pressure determining means 138 and respective prescribed time periods preceding and following the blood-pressure-measurement period. FIG. 7 shows an example of the relationship between blood pressure and magnitude of pressure pulse wave. In FIG. 7, symbols $PW_{min}$, $PW_{max}$ indicate a minimal magnitude (i.e., a magnitude of a rising point) and a maximal magnitude (i.e., a magnitude of a peak point) of a heartbeat-synchronous pulse of the radial-artery pressure pulse wave PW, respectively. The time periods preceding and following the blood-pressure-measurement period are so prescribed that in each of those time periods the blood pressure of the patient does not change so largely from that in the blood-pressure-measurement period, and may include respective time periods immediately before and after the blood-pressure-measurement period. In particular, in the case where the cuff 52 and the pressure-pulse-wave detecting probe 12 are worn on a common arm of the patient, the radial-artery pressure pulse wave PW is obtained in a state in which the pressing pressure of the large cuff 58 (hereinafter, referred to as the large-cuff pressure PC1) is lower than a prescribed pressure at which the large cuff 58 starts blocking the flow of blood in the arm.

A blood-pressure monitoring means 142 successively determines, according to the relationship between blood pressure and magnitude of pressure pulse wave, determined by the first relationship determining means 140, a monitor blood pressure MBP of the patient based on a magnitude of each of respective heartbeat-synchronous pulses of the radial-artery pressure pulse wave PW detected by the active element of the second pressure-pulse-wave sensor 32. More specifically described, the monitoring means 142 successively determines, according to the relationship between blood pressure and pressure-pulse-wave magnitude, a monitor diastolic blood pressure $MBP_{DIA}$ of the patient based on a minimal magnitude $PW_{min}$ of each of the pulses of the radial-artery pressure pulse wave PW, and successively determines, according to the relationship, a monitor systolic blood pressure $MBP_{SYS}$ of the patient based on a maximal magnitude $PW_{max}$ of each of the pulses of the radial-artery pressure pulse wave PW. In addition, the monitoring means 142 operates the display device 120 to display the thus determined monitor diastolic and systolic blood-pressure values $MBP_{DIA}$, $MBP_{SYS}$.

Figure 8:
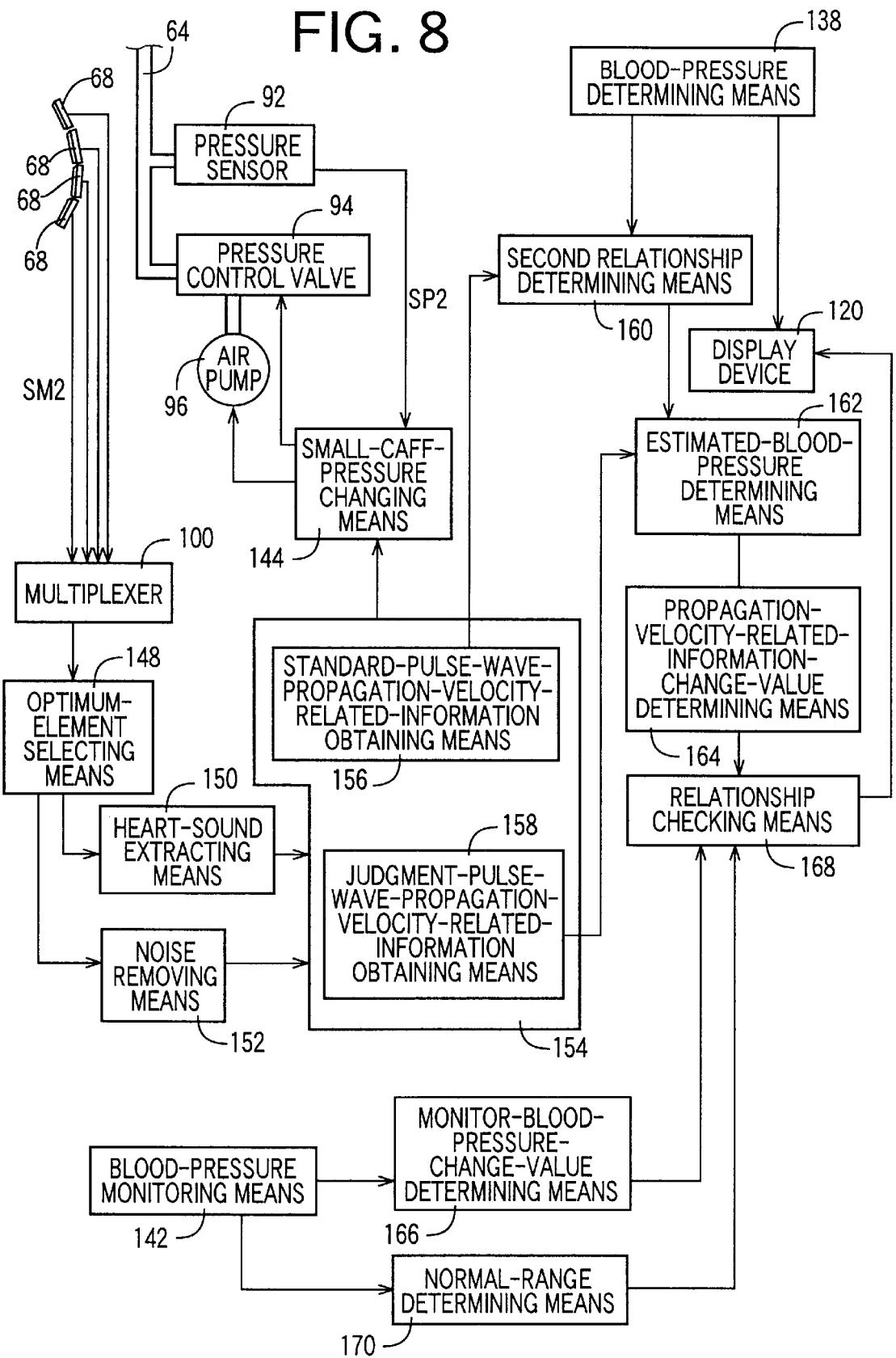
FIG. 8 is a block diagram for explaining essential control functions of the control device that relate to the function of judging whether a second pressure-pulse-wave sensor is appropriately pressed.

FIG. 8 shows a block diagram for explaining essential control functions of the control device 48 that relate to the function of judging whether a condition under which the second pressure-pulse-wave sensor 32 is pressed is appropriate.

A small-cuff-pressure control means 114 controls, based on the second pressure signal SP2 supplied from the pressure sensor 92, the pressure control valve 94 and the air pump 96 to increase the air pressure $P_{K2}$ in the small cuff 60 up to a prescribed target pressure PM2 and then keep the pressure $P_{K2}$ at the target pressure PM2. The target pressure PM2 is prescribed at such a value which assures that the press surface 70 which is provided on the inner surface of the cuff 12 and to which the first pressure-pulse-wave sensors 68 are fixed, is pressed against the upper arm 54, but does not occlude the flow of blood through a brachial artery 146 of the upper arm 54.

Figure 9:
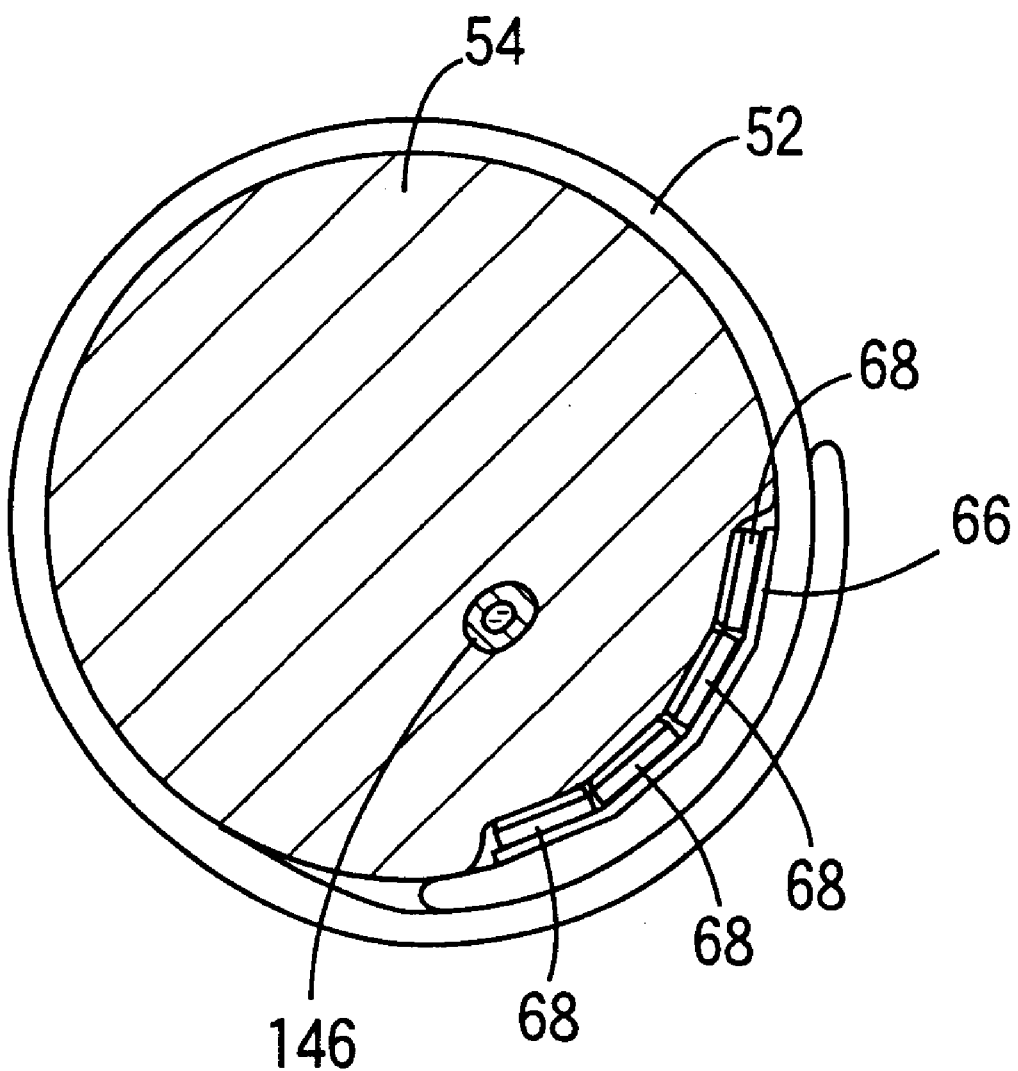
FIG. 9 is a cross-section view for explaining a state in which a cuff is wound around an upper arm of a living subject.
Figure 10:
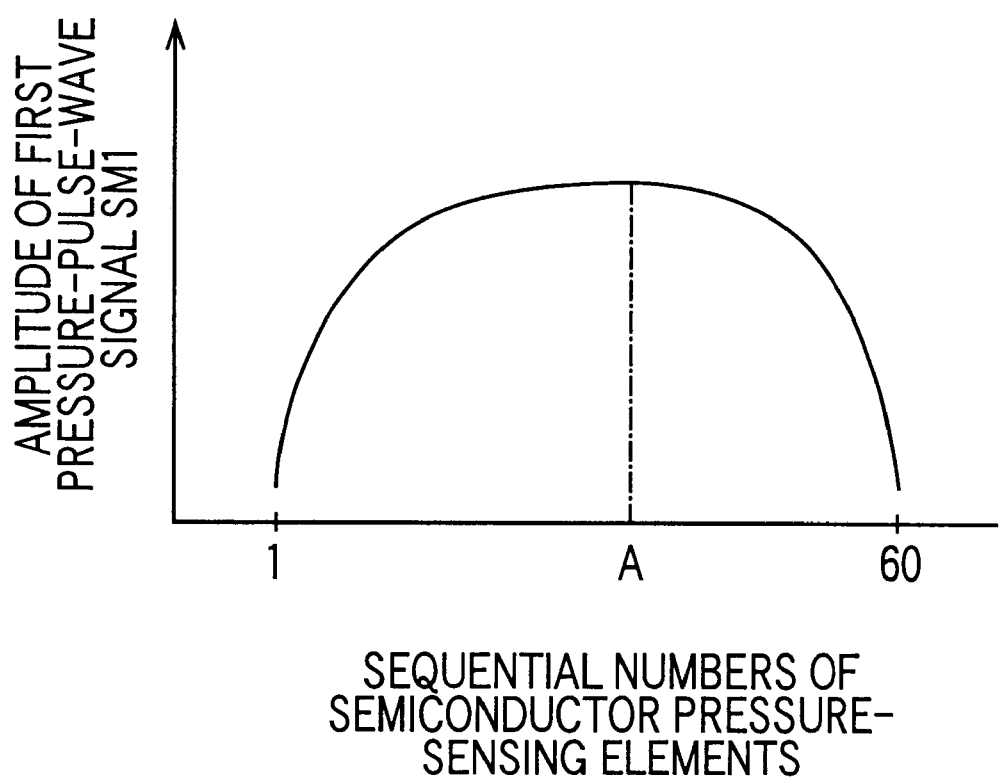
FIG. 10 is a graph showing a relationship between individual pressure-sensing semiconductor elements of first pressure-pulse-wave sensors and respective amplitudes of respective first pressure-pulse-wave signals SM1 generated by the individual pressure-sensing elements.

An optimum-element selecting means 148 selects, from the sixty pressure-sensing semiconductor elements 72 of the four pressure-pulse-wave sensors 68, an optimum pressure-sensing element 72 that is the most appropriate to detect heart sounds (hereinafter, referred to as the optimum element A). FIG. 9 is a cross-section view showing the state in which the cuff 52 is wound around the upper arm 54. As shown in FIG. 9, the pressure-sensing elements 72 provided on the press surfaces 70 of the pressure-pulse-wave sensors 68 have respective different distances from the brachial artery 146 of the upper arm 54. Therefore, it is desirable that one of the pressure-sensing elements 72 that is located right above, or in the vicinity of, the brachial artery 146 be selected as the optimum element A that can detect, with the highest sensitivity, the brachial-artery pressure pulse wave. FIG. 10 shows a relationship between the pressure-sensing elements 72 and respective amplitudes of the first pressure-pulse-wave signals SM1 detected by the elements 72. In FIG. 10, the sequential numbers of the pressure-sensing elements 72 start with one of opposite ends of the array of elements 72 provided on the press surfaces 70. Respective amplitudes of first pressure-pulse-wave signals SM1 detected by nearer pressure-sensing elements 72 to the brachial artery 146 are greater than those detected by remoter elements 72 from the artery 146. Therefore, the optimum-element selecting means 148 selects, as the optimum element A, one of the pressure-sensing elements 72 that provides a first pressure-pulse-wave signal SM1 having a greater amplitude in the relationship shown in FIG. 10, most preferably, the element 72 that provides the first signal SM1 having the greatest amplitude.

A heart-sound extracting means 150 subjects the first pressure-pulse-wave signal SM1 supplied from the optimum element A, to a digital filter, and thereby extracts, from the first signal SM1, a heart-sound component having frequencies in a prescribed frequency band corresponding to a frequency band generally possessed by heart sounds. The prescribed frequency band may range from 30 to 600 Hz. A main component of the first pressure-pulse-wave signal SM1 is the brachial-artery pressure pulse wave BAP produced from the pulsation of the brachial artery 146. However, heart sounds, produced when the valves of the heart open and close, propagate through the blood vessels. Therefore, the first pressure-pulse-wave signal SM1 contains the heart-sound component. Thus, the heart sounds can be detected at the upper arm 54 by extracting, from the first pressure-pulse-wave signal SM1, a signal having frequencies in the frequency band generally had by the heart sounds.

Figure 11:
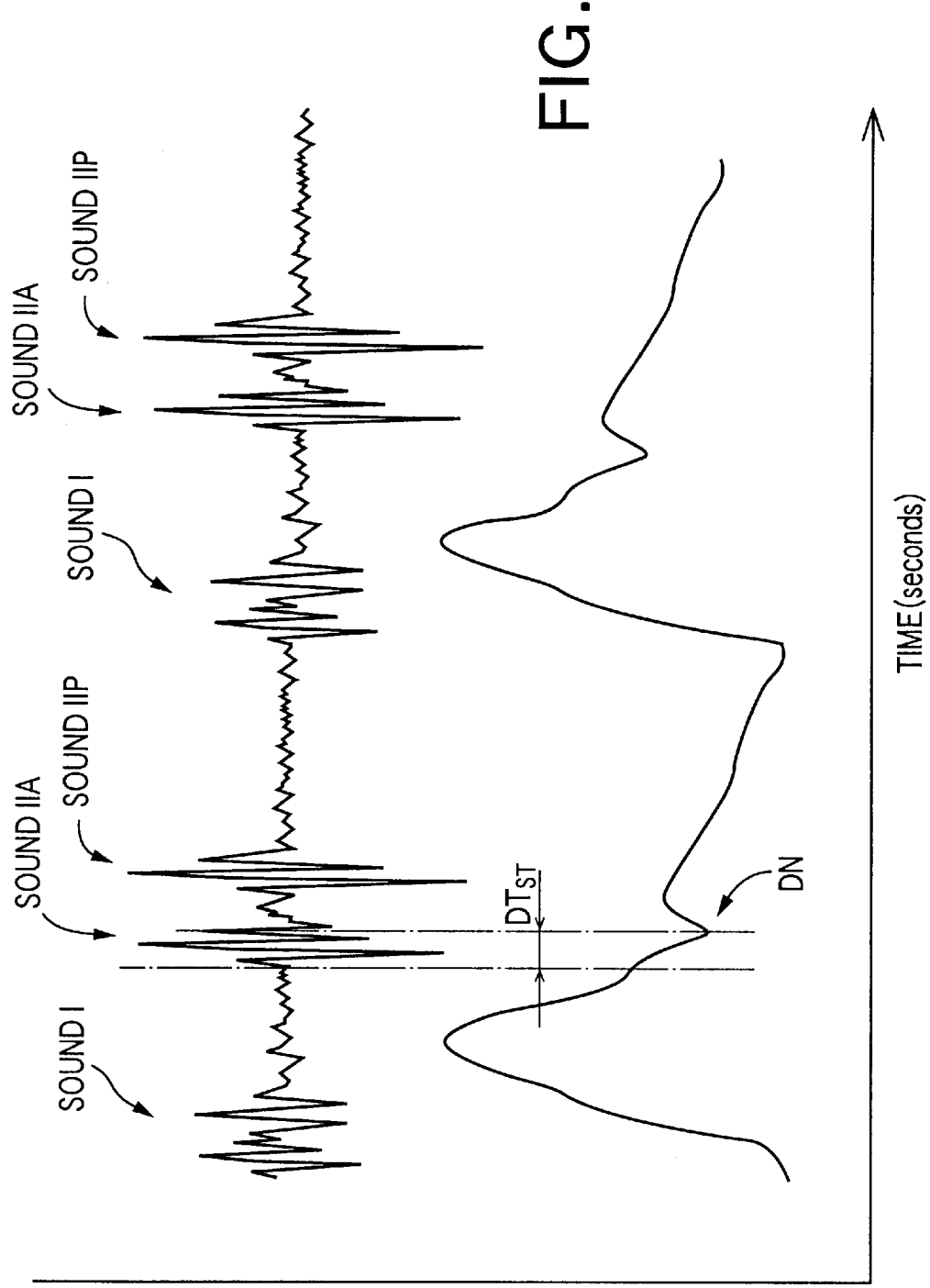
FIG. 11 is a graph showing heart sounds extracted by a heart-sound extracting means, and a brachial-artery pressure pulse wave BAP from which noise has been extracted by a noise removing means.

A noise removing means 152 subjects the first pressure-pulse-wave signal SM1 supplied from the optimum element A, to a digital filter, and thereby removes noise from the first signal SM1, so as to extract the brachial-artery pressure pulse wave BAP produced by the brachial artery 146. Since the brachial-artery pressure pulse wave BAP is a heartbeat-synchronous wave, the noise removing means 152 removes, from the first pressure-pulse-wave signal SM, a component having frequencies not lower than 50 Hz. FIG. 11 shows an example of heart sounds extracted by the heart-sound extracting means 150, and an example of a brachial-artery pressure pulse wave BAP from which noise has been removed by the noise removing means 152.

A pulse-wave-propagation-velocity-related information obtaining means 154 includes a standard-pulse-wave-propagation-velocity-related-information obtaining means 156 and a judgment-pulse-wave-propagation-velocity-related-information obtaining means 158. The standard-pulse-wave-propagation-velocity-related-information obtaining means 156 obtains, as a piece of standard pulse-wave-propagation-velocity-related information, a piece of pulse-wave-propagation-velocity-related information, at a time in the above-described, prescribed time duration consisting of the blood-pressure-measurement period of the blood-pressure determining means 138 and the respective time periods preceding and following the blood-pressure-measurement period, so that a second relationship determining means 160, described below, may determines a relationship between blood pressure and pulse-wave-propagation-velocity-related-information, based on the blood-pressure value BP determined by the blood-pressure determining means 138 and the thus obtained piece of standard pulse-wave-propagation-velocity-related information.

More specifically described, the standard-pulse-wave-propagation-velocity-related-information obtaining means 156 operates, at a time in the prescribed time duration consisting of the blood-pressure-measurement period of the blood-pressure determining means 138 (only in a state in which the large-cuff pressure PC1 is lower than the target pressure PM2) and the respective time periods preceding and following the blood-pressure-measurement period, the small-cuff-pressure changing means 144 to keep the pressure $P_{K2}$ in the small cuff 60 at the target pressure PM2, so that in this state the heart-sound extracting means 150 may extract the heart sounds and the noise removing means 152 may remove noise from the brachial-artery pressure pulse wave BAP. Then, the standard-pulse-wave-propagation-velocity-related-information obtaining means 156 determines, as a standard pulse-wave propagation time $DT_{ST}$ (sec), a time difference between a time of detection of a prescribed periodic point on the heart sounds, and a time of detection of a prescribed periodic point on the brachial-artery pressure pulse wave BAP. The prescribed periodic point of the heart sounds may be a starting point (i.e., a rising point) of a first heart sound I, a peak point of the first heart sound I, a starting point of a second heart sound IIA, or a peak point of the second heart sound IIA. The prescribed periodic point of the brachial-artery pressure pulse wave BAP may be a periodic point corresponding to the periodic point of the heart sounds. For example, the second heart sound IIA is a sound produced when the aortic valve closes, and corresponds to a notch DN occurring to the brachial-artery pressure pulse wave BAP. FIG. 11 shows a manner in which a standard pulse-wave propagation time $DT_{ST}$ is determined as a time difference between the time of detection of the rising point of the second heart sound IIA and the time of detection of the notch DN of the brachial-artery pressure pulse wave BAP.

In addition, the standard-pulse-wave-propagation-velocity-related-information obtaining means 156 determines, based on the thus determined standard pulse-wave propagation time $DT_{ST}$, a standard pulse-wave propagation velocity $PWV_{ST}$ (cm/sec), according to the following expression (1) pre-stored in the ROM 116:

$$PWV_{ST}=L/DT_{ST} \qquad (1)$$

where L (m) is a constant value representing a length of the blood vessel from the initial portion of the aorta to the position where the optimum element A is worn, and is experimentally obtained in advance.

The judgment-pulse-wave-propagation-velocity-related-information obtaining means 158 operates, at a prescribed judgment period Ta (e.g., 2.5 to 5 minutes) shorter than the calibration period Tc, the small-cuff-pressure changing means 144 to keep the pressure $P_{K2}$ in the small cuff 60 at the target pressure PM2, so that, in this state, the heart-sound extracting means 150 may extract the heart sounds and the noise removing means 152 may remove noise from the brachial-artery pressure pulse wave BAP. Like the standard-pulse-wave-propagation-velocity-related-information obtaining means 156, the judgment pulse-wave-propagation-velocity-related-information obtaining means 158 determines a judgment pulse-wave propagation time $DT_2$ and a judgment pulse-wave propagation velocity $PWV_2$. The judgment period Ta is measured from the end of each blood-pressure-measuring operation of the blood-pressure determining means 138.

The second relationship determining means 160 determines two constants $\alpha 1$, $\beta 1$ of the following expression (2) representing a relationship between blood pressure and pulse-ave propagation time, or two constants $\alpha 2$, $\beta 2$ of the following expression (3) representing a relationship between blood pressure and pulse-wave propagation velocity, based on a plurality of blood-pressure values BP (e.g., systolic blood-pressure values $BP_{SYS}$, mean blood-pressure values $BP_{MEAN}$, or diastolic blood-pressure values $BP_{DIA}$) determined by the blood-pressure determining means 138 and a plurality of pieces of standard pulse-wave-propagation-velocity-relate d information obtained by the standard-pulse-wave-propagation-velocity-related-information obtaining means 156:

$$EBP=\alpha 1\ (DT)+\beta 1 \qquad (2)$$

where $\alpha 1$ is a negative constant and $\beta 1$ is a positive constant.

$$EBP=\alpha 2(PWV)+\beta 2 \qquad (3)$$

where $\alpha 2$ is a positive constant and $\beta 2$ is a positive constant.

For example, based on a first combination of the systolic blood-pressure value $BP_{SYS}$ determined by the blood-pressure determining means 138 in a current blood-pressure measuring operation and the pulse-wave propagation time DT obtained during the current blood-pressure measuring operation, and a second combination of the systolic blood-pressure value $BP_{SYS}$ determined by the blood-pressure determining means 138 in its preceding blood-pressure measuring operation and the pulse-wave propagation time DT obtained during the preceding blood-pressure measuring operation, the second relationship determining means 160 determines the two constants $\alpha 1$, $\beta 1$ of the expression (2).

An estimated-blood-pressure determining means 162 determines, based on a piece of judgment pulse-wave-propagation-velocity-related information obtained by the judgment-pulse-wave-propagation-velocity-related-information obtaining means 158, an estimated blood-pressure value EBP of the patient, according to the relationship between blood pressure and pulse-wave-propagation-velocity-related information, i.e., the relationship represented by the expression (2) or the expression (3). In the case where the second relationship determining means 160 determines the constants of the expression (2) or the expression (3), based on the systolic blood-pressure values $BP_{SYS}$, the estimated-blood-pressure determining means 162 determines an estimated systolic blood-pressure value $EBP_{SYS}$ of the patient; in the case where the means 160 determines the constants of the expression (2) or the expression (3), based on the mean blood-pressure values $BP_{MEAN}$, the means 162 determines an estimated mean blood-pressure value $EBP_{MEAN}$ of the patient; and in the case where the means 160 determines the constants of the expression (2) or the expression (3), based on the diastolic blood-pressure values $BP_{DIA}$, the means 162 determines an estimated diastolic blood-pressure value $EBP_{MEAN}$ of the patient.

A propagation-velocity-related-information-change-value determining means 164 determines, each time the judgment period Ta periodically elapses after the last blood-pressure measuring operation, a change value of the pieces of pulse-wave-propagation-velocity-related information obtained by the pulse-wave-propagation-velocity-related-information obtaining means 154. Here, the propagation-velocity-related-information change value is defined as a change rate or a change amount of a current piece of judgment pulse-wave-propagation-velocity-related information, obtained at a current time when the judgment period Ta has elapsed, from its preceding piece of judgment pulse-wave-propagation-velocity-related information, obtained at its preceding time when the judgment period Ta had elapsed, or from the piece of standard pulse-wave-propagation-velocity-related information, obtained during the last blood-pressure measuring operation. Since the standard pulse-wave-propagation-velocity-related information is related to the blood pressure BP by the second relationship determining means 160 and the judgment pulse-wave-propagation-velocity-related information is converted into the estimated blood pressure EBP by the estimated-blood-pressure determining means 162, the propagation-velocity-related-information change values may be obtained as change values determined based on the blood-pressure value BP and the estimated blood-pressure values EBP.

A monitor-blood-pressure-change-value determining means 166 determines, each time the judgment period Ta periodically elapses, a change value of the monitor blood-pressure values determined by the blood-pressure monitoring means 142 at respective times when the pieces of pulse-wave-propagation-velocity-related information used to determine the propagation-velocity-related-information change values are obtained.

A relationship checking means 168 compares the propagation-velocity-related-information change value determined by the propagation-velocity-related-information-change-value determining means 164, and the monitor-blood-pressure change value determined by the monitor-blood-pressure-change-value determining means 166, with each other, and judges whether the relationship between blood pressure and pressure pulse wave, determined by the first relationship determining means 140, is appropriate. If the relationship is not appropriate because the second pressure-pulse-wave sensor 32 is not appropriately pressed, the monitor blood-pressure values MBP determined by the blood-pressure monitoring means 142 may largely differ from the actual blood pressure of the patient. On the other hand, though the pulse-wave-propagation-velocity-related information is less accurate than the monitor blood-pressure values MBP, the information changes in relation with the change of blood pressure of the patient, and is obtained based on the time difference between the respective periodic points of the heart sounds and the brachial-artery pressure pulse wave BAP. Thus, the pulse-wave-propagation-velocity-related information is not influenced by the state in which the second pressure-pulse-wave sensor 32 is pressed. Therefore, it is possible to judge whether the relationship between blood pressure and pressure pulse wave is appropriate, by comparing the propagation-velocity-related-information change value and the monitor-blood-pressure change value with each other. For example, if a relative value of the monitor-blood-pressure change value relative to the propagation-velocity-related-information change value does not fall within a predetermined normal range, the relationship checking means 168 judges that the relationship between blood pressure and pressure pulse wave is not appropriate. The relative value of the monitor-blood-pressure change value may be a difference of the monitor-blood-pressure change value from the propagation-velocity-related-information change value, or a ratio of the monitor-blood-pressure change value to the propagation-velocity-related-information change value. In the case where the relative value of the monitor-blood-pressure change value relative to the propagation-velocity-related-information change-value is obtained as the ratio of the monitor-blood-pressure change value to the propagation-velocity-related-information change value, the normal range may range from 0.8 to 1.2.

A normal-range determining means 170 determines, as the normal range, a narrower range, if the estimated diastolic blood-pressure value $MBP_{DIA}$ determined by the blood-pressure monitoring means 142 when the relationship checking means 168 checks the relationship between blood pressure and pressure pulse wave is smaller than a prescribed danger value (e.g., 70 mmHg) which indicates that the patient needs an urgent treatment. For example, in the case where the normal range ranges from 0.8 to 1.2 as described above, the normal-range determining means 170 narrows the normal range into the narrower range of 0.85 to 1.15.

Figure 12:
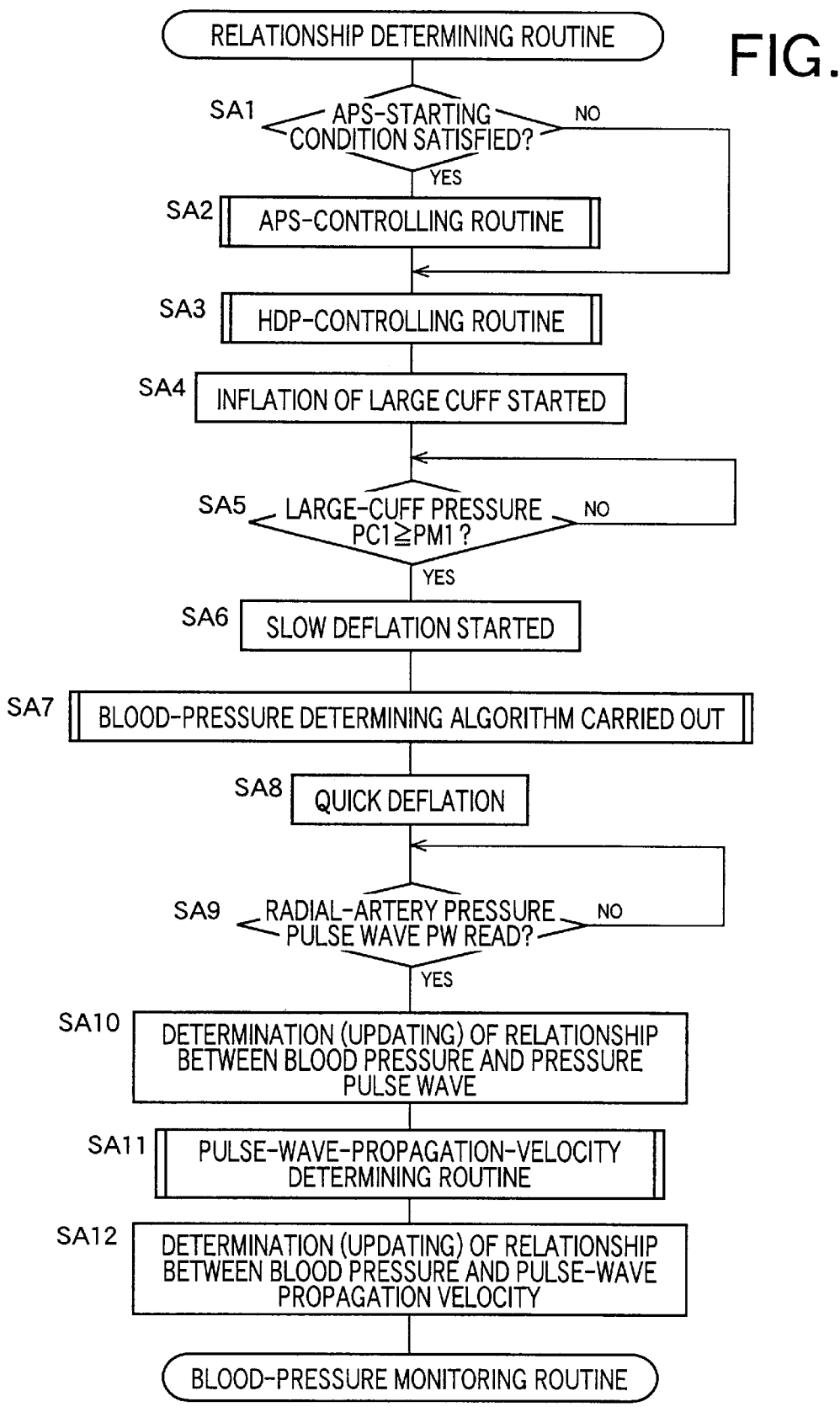
FIG. 12 is a flow chart representing a relationship determining routine according to which the control device shown in FIG. 1 determines a relationship between blood pressure and pressure pulse wave, and a relationship between blood pressure and pulse-wave propagation velocity.
Figure 13:
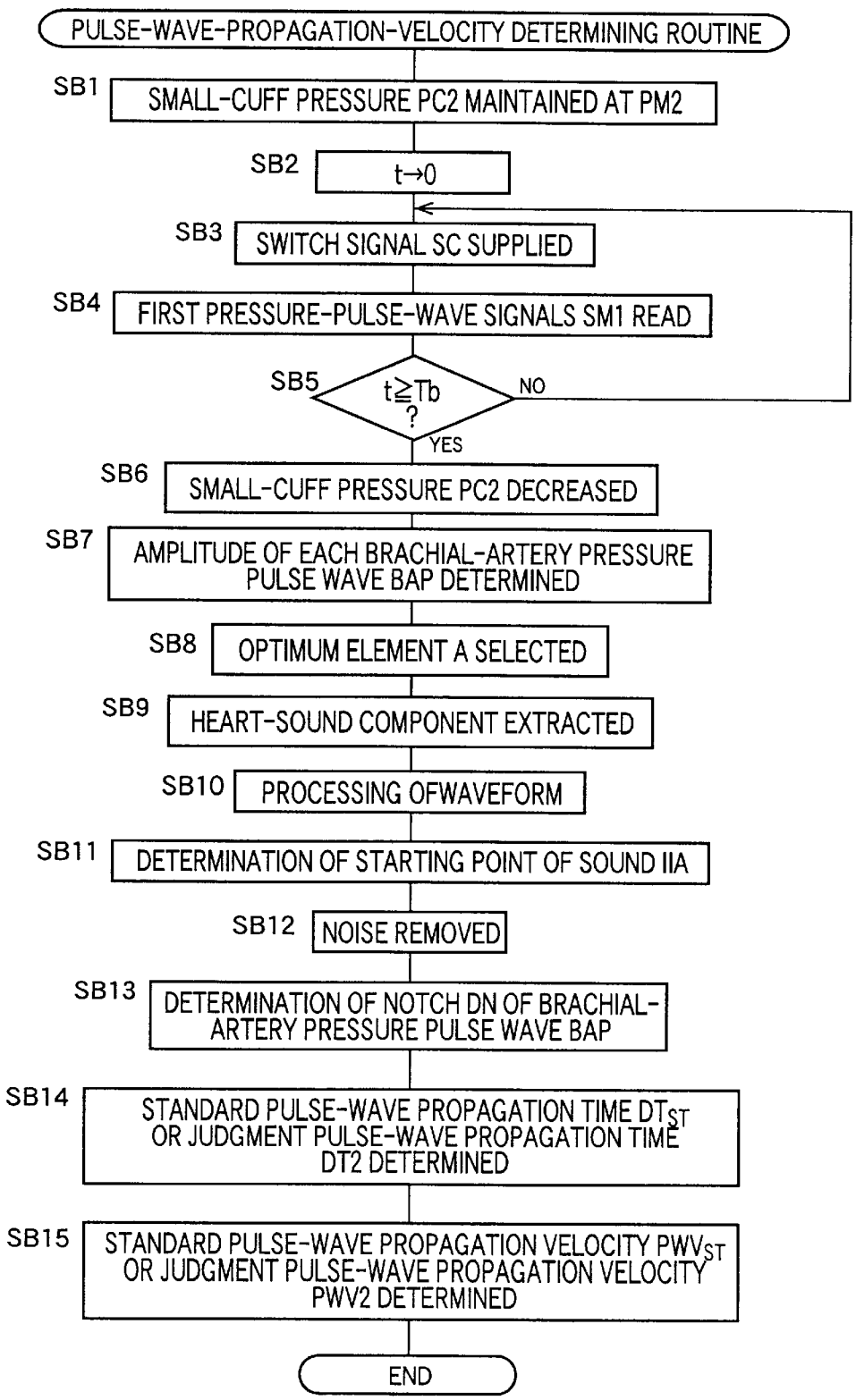
FIG. 13 is a flow chart representing a pulse-wave-propagation-velocity determining routine according to which the control device of FIG. 1 determines a pulse-wave-propagation velocity PWV.
Figure 14:
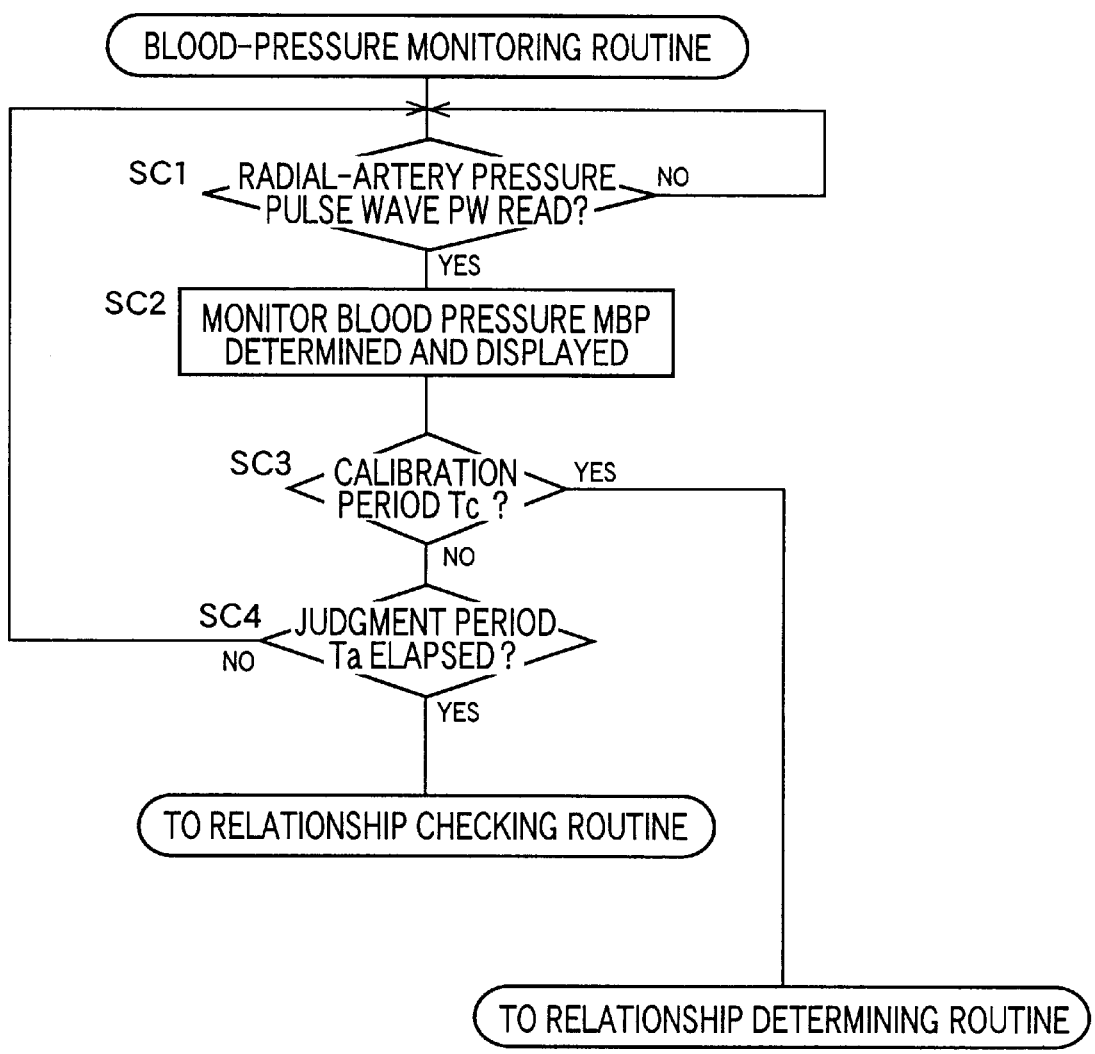
FIG. 14 is a flow chart representing a blood-pressure monitoring routine according to which the control device of FIG. 1 successively determines a monitor blood-pressure value MBP.
Figure 15:
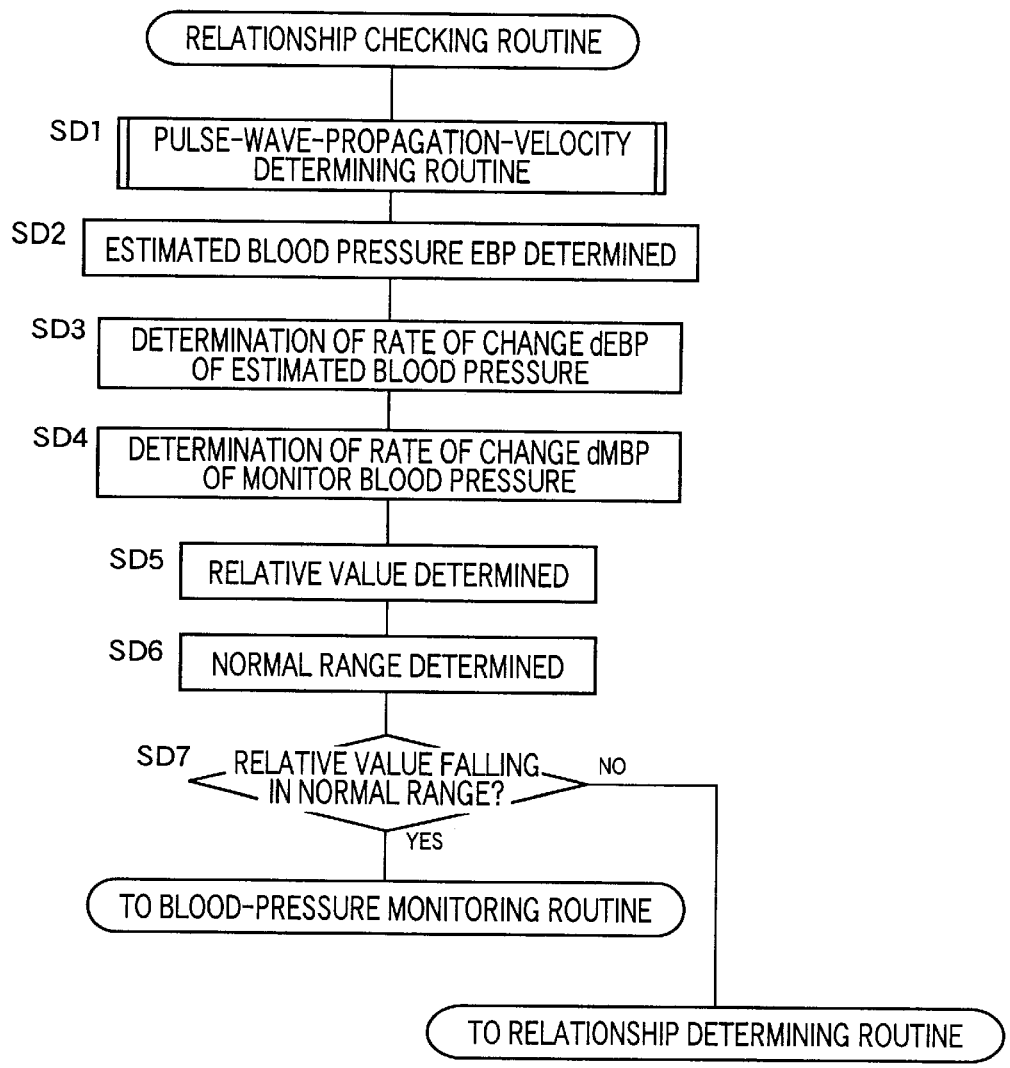
FIG. 15 is a flow chart representing a relationship checking routine according to which the control device of FIG. 1 judges whether the relationship between blood pressure and pressure pulse wave is appropriate.

FIGS. 12, 13, 14, and 15 are flow charts representing essential control functions of the control device 48 shown in FIGS. 5 and 8. FIG. 12 shows a relationship determining routine for determining a relationship between blood pressure and pressure pulse wave, and a relationship between blood pressure and pulse-wave propagation velocity; FIG. 13 shows a pulse-wave-propagation-velocity determining routine for determining a pulse-wave-propagation velocity PWV; FIG. 14 shows a blood-pressure monitoring routine for continuously determining monitor blood-pressure values MBP of a patient; and FIG. 15 shows a relationship checking routine for judging whether the relationship between blood pressure and pressure pulse wave is appropriate.

According to the relationship determining routine of FIG. 12, first, the control device 48 carries out Step SA1 (hereinafter, "Step" is omitted, if appropriate) where the control device 48 judges whether the prescribed pressing-position changing condition (i.e., the APS-starting condition) has been satisfied, for example, whether one of the pressure-sensing elements, arranged on the press surface 40 of the second pressure-pulse-wave sensor 32, that detects the greatest one of the respective amplitudes of the respective pressure pulse waves detected by all the elements is located in either one of the opposite end portions of the array of elements.

If the pressing position where the second pressure-pulse-wave sensor 32 is pressed against the radial artery 18 is not appropriate, for example, when the pressure-pulse-wave detecting probe 12 is initially worn on the patient, and accordingly if the prescribed pressing-position changing condition is satisfied, a positive judgment is made at SA1, so that the control proceeds with SA2, i.e., an APS-controlling routine. According to this APS-controlling routine, the control device 48 determines an optimum pressing position where one of the pressure-sensing elements that is located at substantially the middle of the array of elements detects the greatest one of the respective amplitudes of the respective pressure pulse waves detected by all the elements, that is, where one of the pressure-sensing elements that detects the greatest one of the respective amplitudes of the respective pressure pulse waves detected by all the elements, is located at substantially the middle of the array of elements. In addition, the control device 48 determines, as an active element, the one pressure-sensing element located at substantially the middle of the array of elements. Since at SA1 and SA2, the pressing position where the second pressure-pulse-wave sensor 32 is pressed is determined, SA1 and SA2 correspond to the optimum-pressing-position determining means 130.

On the other hand, if a negative judgment is made at SA1 because the second pressure-pulse-wave sensor 32 is appropriately positioned relative to the radial artery 18, or after SA2, the control goes to SA3, i.e., an HDP-controlling routine corresponding to the optimum-pressing-force determining means 132 and the optimum-pressing-force maintaining means 134.

More specifically described, the control device 48 continuously increases the pressing force $P_{HDP}$ applied to the second pressure-pulse-wave sensor 32, and determines, as an optimum pressing force $P_{HDPO}$, a value of the pressing force $P_{HDP}$ at the time when the active element of the second sensor 32, positioned right above the radial artery 18, detects the greatest one of respective amplitudes of respective heartbeat-synchronous pulses of the pressure pulse wave PW(t), and replaces the prior optimum pressing force with the thus determined new optimum pressing force $P_{HDPO}$. Then, the pressing force $P_{HDP}$ applied to the second sensor 32 is maintained at the new optimum pressing force $P_{HDPO}$.

Subsequently, at SA4, the control device 48 switches the deflation control valve 76 to its pressure-supply position, and operates the air pump 78, so that the increasing of the pressure in the large cuff 58 is started. At SA5, the control device 48 judges whether the pressure PC1 of the large cuff 58 has reached a prescribed target pressure PM1, i.e., 180 mmHg. If a negative judgment is made at SA5, SA5 is repeated. If a positive judgment is made at SA5, then the control goes to SA6 to stop the air pump 78 and switch the deflation control valve 76 to its slow-deflation position, so that the large-cuff pressure PC1 is slowly decreased at a prescribed rate of 5 mmHg/sec.

Then, at SA7 corresponding to the blood-pressure determining means 138, the control device 48 determines a systolic blood-pressure value $BP_{SYS}$, a mean blood-pressure value $BP_{MEAN}$, and a diastolic blood-pressure value $BP_{DIA}$ of the patient, based on the change of respective amplitudes of respective heartbeat-synchronous pulses of the cuff pulse wave KW represented by the cuff-pulse-wave signal SW continuously obtained during the slow decreasing of the large-cuff pressure PC1, according to well-known oscillometric-type blood-pressure determining algorithm. The thus determines blood-pressure values BP are displayed on the display device 120. Then, at SA8, the control device 48 switches the deflation control valve 76 to its quick-deflation position, so that the pressure in the large cuff 58 is quickly released. Thus, SA4 to SA6 and SA8 correspond to the large-cuff-pressure changing means 136.

Then, at SA9, the control device 48 reads in a length of the radial-artery pressure pulse wave PW(t), detected by the second pressure-pulse-wave sensor 32, that corresponds to one heartbeat of the patient. If a negative judgment is made at SA9, SA9 is repeated. Meanwhile, if a positive judgment is made at SA9, the control goes to SA10 corresponding to the first relationship determining means 140. At SA10, the control device 48 determines or updates the relationship between blood pressure and pressure pulse wave, shown in FIG. 6, based on a minimal magnitude $PW_{min}$ and a maximal magnitude $PW_{max}$ of the one heartbeat-synchronous pulse of the radial-artery pressure pulse wave PW read in at SA9, and the diastolic and systolic blood-pressure values $BP_{DIA}$, $BP_{SYS}$ determined at SA7.

Then, at SA11, the control device 48 carries out the pulse-wave-propagation-velocity determining routine of FIG. 13, so as to determine a pulse-wave-propagation velocity PWV. This pulse-wave-propagation-velocity determining routine is also carried out in the relationship checking routine, described later.

In FIG. 13, first, at Step SB1 corresponding to the small-cuff-pressure changing means 144, the control device 48 starts the air pump 96 and operates the pressure control valve 94, so that the pressure in the small cuff 60 (hereinafter, referred as to the "small-cuff pressure PC2") is kept at a prescribed target pressure PM2, i.e., 40 mmHg.

Next, at SB2, a content of a timer t is replaced with "0", so that the timer t is reset to zero and, at SB3, the control device 48 outputs the switch signals SC to switch the multiplexer 100 and the EPROM 104 at a period sufficiently shorter than an average pulse period. Then, at SB4, the control device 48 reads in the first pressure-pulse-wave signal SM1 supplied from the multiplexer 100.

Next, at SB5, the control device 48 judges whether a time indicated by a number counted by the timer t; has reached a prescribed reading-in period Tb The reading-in period Tb may be equal to an average pulse period, i.e., a length of one average heartbeat-synchronous pulse. Each time one switch signal SC is supplied to the multiplexer 100 at SB3, one of the respective first pressure-pulse-wave signals SM1 detected by the sixty pressure-sensing elements 72 is supplied from the multiplexer 100 to the control device 48. While SB3 to SB5 are repeated sixty times, all the first signals SM1 detected by the sixty elements 72 are supplied from the multiplexer 100 to the control device 48.

If a positive judgment is made at SB5, the control device 48 carries out SB6 corresponding to the small-cuff-pressure changing means 144, where the control device 48 stops the air pump 96 and switches the pressure control valve 94 to its quick-deflation position, so that the pressure in the small cuff 60 is released.

Next, the control goes to SB7 and SB8 corresponding to the optimum-element selecting means 148. At SB7, the control device 48 determines respective amplitudes of the respective brachial-artery pressure pulse waves BAP which have been read in while SB3 to SB5 are repeated. At SB8, the control device 48 determines the greatest one of the respective amplitudes determined at SB7, and determines, as the optimum element A, one of the pressure-sensing elements 72 that provides the greatest amplitude.

Next, the control goes to SB9 corresponding to the heart-sound extracting means 150. At SB9, the control device 48 subjects the first pressure-pulse-wave signal SM1 detected by the optimum element A selected at SB8, to a digital filter, so as to extract a component having frequencies of from 30 to 600 Hz. Thus, the heart-sound component is extracted from the first pressure-pulse-wave signal SM1.

At SB10, the control device 48 processes a waveform of the heart-sound component extracted at SB9, so as to determine a prescribed periodic point on the waveform as one of two reference points to determine a pulse-wave propagation time DT. More specifically described, the waveform of the heart-sound component is subjected to a smoothing or differentiating process which is known as a useful technique to process a physical signal, and the thus processed waveform is further subjected to a squaring process. Thus, the amplitude of the waveform of heart sounds, measured from a baseline representing a signal level when no heart sounds are detected, is squared.

Next, at SB11, the control device 48 determines, based on the waveform whose amplitude has been squared at SB10, a starting point of a second heart sound IIA as the first reference point to determine the pulse-wave propagation time DT. Then, at SB12 corresponding to the noise removing means 162, the control device 48 subjects the first pressure-pulse-wave signal SM1 detected by the optimum element A, to a digital filter to remove a component having frequencies not lower than 50 Hz. Thus, a brachial-artery pressure pulse wave BAP free of noise is extracted from the first pressure-pulse-wave signal SM1.

Subsequently, at SB13, the control device 48 determines, based on the brachial-artery pressure pulse wave BAP extracted at SB12, a notch DN of the pulse wave BAP that corresponds to the starting point of the second heart sound IIA. The notch DN of the pulse wave BAP is the second reference point to determine the pulse-wave propagation time DT. This notch DN may be determined by identifying a point, on the brachial-artery pressure pulse wave BAP extracted at SB12, where the magnitude of the pulse wave BAP that decreases after a peak point changes to increase.

Then, the control goes to SB14 and SB15 corresponding to the pulse-wave-propagation-velocity-related-information obtaining means 154. In the case where the pulse-wave-propagation-velocity determining routine of FIG. 13 is carried out as part of the relationship determining routine of FIG. 12, SB14 and SB15 of this routine correspond to the standard-pulse-wave-propagation-velocity-related-information obtaining means 156 which determines a standard pulse-wave-propagation velocity $PWV_{ST}$. Meanwhile, In the case where the pulse-wave-propagation-velocity determining routine of FIG. 13 is carried out as part of the relationship checking routine of FIG. 15, SB14 and SB15 of this routine correspond to the judgment-pulse-wave-propagation-velocity-related-information obtaining means 158 which determines a judgment pulse-wave-propagation velocity PWV2.

At SB14, the control device 48 determines a time difference DT between a time of detection of the starting point of the second heart sound IIA determined at SB11 and a time of detection of the notch DN of the brachial-artery pressure pulse wave BAP determined at SB13. The thus determined time difference DT is used as a standard pulse-wave propagation time $DT_{ST}$ or a judgment pulse-wave propagation time DT2.

At SB15, the control device 48 determines a standard pulse-wave propagation velocity $PWV_{ST}$ or a judgment pulse-wave propagation velocity PWV2, by replacing the parameter DT of the expression (1) with the time difference DT determined at SB14.

Back to FIG. 12, the pulse-wave-propagation-velocity determining routine of SA11 is followed by SA12 corresponding to the second relationship determining means 160. At SA12, the control device 48 determines or updates the constant values $\alpha 2$, $\beta 2$ of the expression (3), based on a first combination of the standard pulse-wave propagation velocity $PWV_{ST}$ determined at SA11, and the diastolic blood-pressure value $BP_{DIA}$ determined at SA7, in the current control cycle according to this relationship determining routine, and a second combination of the standard pulse-wave propagation velocity $PWV_{ST}$ determined at SA11, and the diastolic blood-pressure value $BP_{DIA}$ determined at SA7, in the preceding control cycle according to this routine. In the case where the current control cycle is an initial control cycle according to this routine, the control device 48 employs, as the above-indicated second combination, a standard combination of a standard pulse-wave propagation velocity $PWV_{ST}$ and a diastolic blood-pressure value $BP_{DIA}$ that is pre-stored in the ROM 104. SA12 is followed by the blood-pressure monitoring routine of FIG. 14.

Next, the blood-pressure monitoring routine of FIG. 14 will be described. At SC1 of FIG. 14, the control device 48 judges whether the control device has read in one heartbeat-synchronous pulse of the radial-artery pressure pulse wave PW(t). If a negative judgment is made at SC1, SC1 is repeated. Meanwhile, if a positive judgment is made at SC1, the control goes to SC2 corresponding to the blood-pressure monitoring means 142.

At SC2, the control device 48 determines, according to the relationship between blood pressure and pressure pulse wave, determined at SA10 of FIG. 12, a monitor diastolic blood-pressure value $MBP_{DIA}$ and a monitor systolic blood-pressure value $MBP_{SYS}$ of the patient, based on a minimal magnitude $PW_{min}$ and a maximal magnitude $PW_{max}$ of the one heartbeat-synchronous pulse of the radial-artery pressure pulse wave PW(t) read in at SC1, and operates the display device 120 to display the thus determined monitor diastolic and systolic blood-pressure values $MBP_{DIA}$, $MBP_{SYS}$.

Then, at SC3, the control device 48 judges whether the prescribed calibration period Tc, e.g., from 10 to 30 minutes has elapsed after the determination of the blood-pressure values BP at SA7 of FIG. 12. If a positive judgment is made at SC3, the control goes to the relationship determining routine of FIG. 12.

On the other hand, if a negative judgment is made at SC3, the control goes to SC4 to judge whether the judgment period Ta, i.e., 2.5 minutes have elapsed after the determination of the blood-pressure values BP at SA7 of FIG. 12, or after the relationship checking routine of FIG. 15, described later, has been carried out. If a negative judgment is made at SC4, the control goes back to SC1 and the following steps. On the other hand, if a positive judgment is made at SC4, the control device 48 carries out the relationship checking routine of FIG. 15.

Next, the relationship checking routine of FIG. 15 will be described. In FIG. 15, first, at SD1, the control device 48 carries out the pulse-wave-propagation-velocity determining routine of FIG. 13, and determines a judgment pulse-wave-propagation velocity PWV2.

Then, at SD2 corresponding to the estimated-blood-pressure determining means 162, the control device 48 determines, according to the expression (3) determined or updated at SA12 of FIG. 12, an estimated diastolic blood pressure $EBP_{DIA}$ of the patient based on the judgment pulse-wave propagation velocity PWV2 determined at SD1.

Subsequently, at SD3, the control device 48 determines a rate of change $dEBP_{DIA}$ of the estimated diastolic blood-pressure value $EBP_{DIA}$ determined at SD2 from the diastolic blood-pressure value $BP_{DIA}$ determined at SA7 of FIG. 12. Since the estimated-diastolic-blood-pressure change rate $dEBP_{DIA}$ is a sort of propagation-velocity-related-information change value, Step SD3 corresponds to the propagation-velocity-related-information-change-value determining means 164.

Then, the control goes to SD4 corresponding to the monitor-blood-pressure-change-value determining means 166. At SD4, the control device 48 determines a rate of change $dMBP_{DIA}$ of the monitor diastolic blood-pressure value $MBP_{DIA}$ determined at SC2 of FIG. 14 from the diastolic blood-pressure value $BP_{DIA}$ determined at SA7 of FIG. 12.

At SD5, the control device 48 determines a ratio of the rate of change $dMBP_{DIA}$ of the monitor diastolic blood-pressure value $MBP_{DIA}$, determined at SD4, to the rate of change $dEBP_{DIA}$ of the estimated diastolic blood-pressure value $EBP_{DIA}$, determined at SD3, as the relative value of the monitor-blood-pressure change value relative to the estimated-blood-pressure change value.

Then, at SD6 corresponding to the normal-range determining means 170, the control device 48 judges whether the monitor diastolic blood-pressure value $MBP_{DIA}$ determined at SC2 of FIG. 14 is smaller than a prescribed danger value, i.e., 70 mmHg and, if a positive judgment is made, narrows the standard normal range of from 0.8 to 1.2 to be used at SD7 to check the relationship between blood pressure and pressure pulse wave, into the narrower normal range of from 0.85 to 1.15.

Then, the control goes to SD7 corresponding to the relationship checking means 168. At SD7, the control device 48 judges whether the relative value (i.e., the ratio) determined at SD5 falls within the standard or narrower normal range determined at SD6. A positive judgment made at SD7 indicates that the relationship between blood pressure and pressure pulse wave is appropriate and accordingly the monitor blood-pressure values MBP are accurate. Therefore, the control goes to the blood-pressure monitoring routine of FIG. 14. On the other hand, a negative judgment made at SD7 indicates that the relationship between blood pressure and pressure pulse wave is not appropriate and accordingly the monitor blood-pressure values MBP are not accurate. Therefore, the control goes to the relationship determining routine of FIG. 12, so that the second pressure-pulse-wave sensor 32 may be appropriately pressed against the radial artery 18 and the relationship between blood pressure and pressure pulse wave is updated.

In the illustrated embodiment in which the above-described flow charts are employed, at SB9 (the heart-sound extracting means 150), the control device 48 extracts the heart-sound component from the brachial-artery pressure pulse wave BAP detected by the first pressure-pulse-wave sensor 68; at SB14 and SB15 (the pulse-wave-propagation-velocity-related-information obtaining means 154), the control device 48 determines the pulse-wave propagation velocity PWV (the standard pulse-wave propagation velocity $PWV_{ST}$ or the judgment pulse-wave propagation velocity PWV2), based on the heart-sound component and the brachial-artery pressure pulse wave BPA; and at SD3 (the propagation-velocity-related-information-change-value determining means 164), the control device 48 determines, at the judgment period Ta, the rate of change dEBP of the estimated blood-pressure value as the relative value of the judgment pulse-wave propagation velocity PWV2. Since the judgment pulse-wave propagation velocity PWV2 changes with the change of blood pressure of the patient, the rate of change dEBP of the estimated blood-pressure value also changes with the change of blood pressure. In addition, the rate of change dMBP of the monitor blood-pressure value determined at SD4 (the monitor-blood-pressure-changevalue determining means 166), also changes with the change of blood pressure. However, in the case where the condition under which the pressure-pulse-wave detecting probe 12 is worn on the patient has changed and the monitor blood-pressure value MBP determined at SC2 (the blood-pressure monitoring means 142) is not accurate, the rate of change dMBP of the monitor blood-pressure value largely differs from the rate of change dEBP of the estimated blood-pressure value. Therefore, at SD7 (the relationship checking means 168), the control device 48 compares the rate of change dMBP of the monitor blood-pressure value and the rate of change dEBP of the estimated blood-pressure value, with each other, and judges whether the relationship between blood pressure and pressure pulse wave, determined at SA10 (the first relationship determining means 140) is appropriate.

Therefore, a longer calibration period Tc can be employed to carry out SA7 (the blood-pressure determining means 138) and thereby update the relationship between blood pressure and pressure pulse wave, and accordingly the discomfort the patient feels can be reduced. Moreover, since the pulse-wave propagation velocity PWV can be determined based on only the signal obtained by the first pressure-pulse-wave sensor 68, the pressure-pulse-wave detecting probe 12 can be worn on the other arm than the arm around which the cuff 52 is wound.

Next, there will be described another or second embodiment of the present invention. The same reference numerals as used in the first embodiment shown in FIGS. 1 to 15 are used to designate the corresponding elements of the second embodiment, and the description thereof is omitted.

Figure 16:
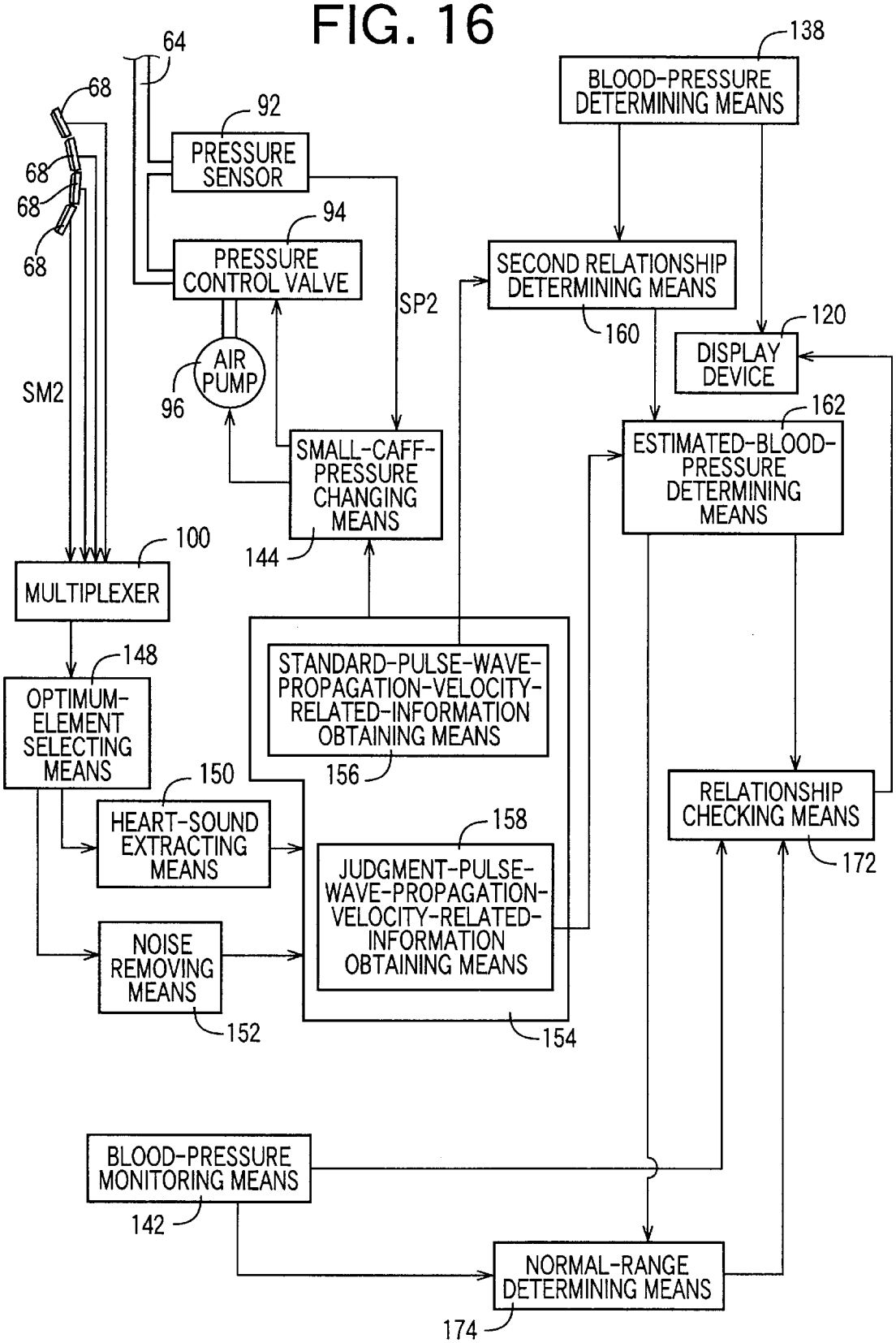
FIG. 16 is a block diagram corresponding to FIG. 8, for explaining essential control functions of another control device of another continuous blood-pressure monitoring apparatus as a second embodiment of the present invention, the control functions relating to the function of judging whether a second pressure-pulse-wave sensor is appropriately pressed.

The second embodiment relates to a continuous blood-pressure monitoring apparatus which differs from the continuous blood-pressure monitoring apparatus 10 shown in FIG. 1 only with respect to control functions of a control device 48 that relate to the function of judging whether a second pressure-pulse-wave sensor 32 is appropriately pressed. FIG. 16 shows a block diagram for explaining essential control functions of the control device 48, employed in the second embodiment, that relate to the function of judging whether the second pressure-pulse-wave sensor 32 is appropriately pressed.

The block diagram shown in FIG. 16 differs from the block diagram shown in FIG. 8, only in that the block diagram of FIG. 16 does not employ the propagation-velocity-related-information-change-value determining means 164 or the monitor-blood-pressure-change-value determining means 166, and employs a relationship checking means 172 and a normal-range determining means 174 in place of the relationship checking means 168 and the normal-range determining means 170 employed in the block diagram of FIG. 8. The relationship checking means 172 and the normal-range determining means 174 will be described below.

The relationship checking means 172 directly compares an estimated blood-pressure value EBP determined by the estimated-blood-pressure determining means 162, and a monitor blood-pressure value MBP determined by the blood-pressure monitoring means 142 based on a magnitude of a heartbeat-synchronous pulse of the radial-artery pressure pulse wave PW detected by the second pressure-pulse-wave sensor 32 at a time around the time of detection of a heartbeat-synchronous pulse of the brachial-artery pressure pulse wave BAP used to determine the estimated blood-pressure value EBP, with each other, and judges whether a relationship between blood pressure and pressure pulse wave, determined by the first relationship determining means 140, is appropriate. For example, the relationship checking means 172 judges that the relationship between blood pressure and pressure pulse wave is not appropriate, if a relative value of the monitor blood-pressure value MBP relative to the estimated blood-pressure value EBP does not fall within a predetermined normal range. The above-indicated relative value may be a difference between the monitor blood-pressure value MBP and the estimated blood-pressure value EBP, or a ratio of one of the two values MBP, EBP to the other. In the case where the ratio is employed as the relative value, the normal range may be predetermined such that the normal range ranges from 0.8 to 1.2.

The normal-range determining means 174 determines a narrower normal range narrower than the above-indicated standard normal range, if at least one of the estimated diastolic blood-pressure value $EBP_{DIA}$ determined by the estimated-blood-pressure determining means 162, and the monitor diastolic blood-pressure value $MBP_{DIA}$ determined by the blood-pressure monitoring means 142 for the checking of the relationship checking means 120 is lower than the previously-explained danger value.

Figure 17:
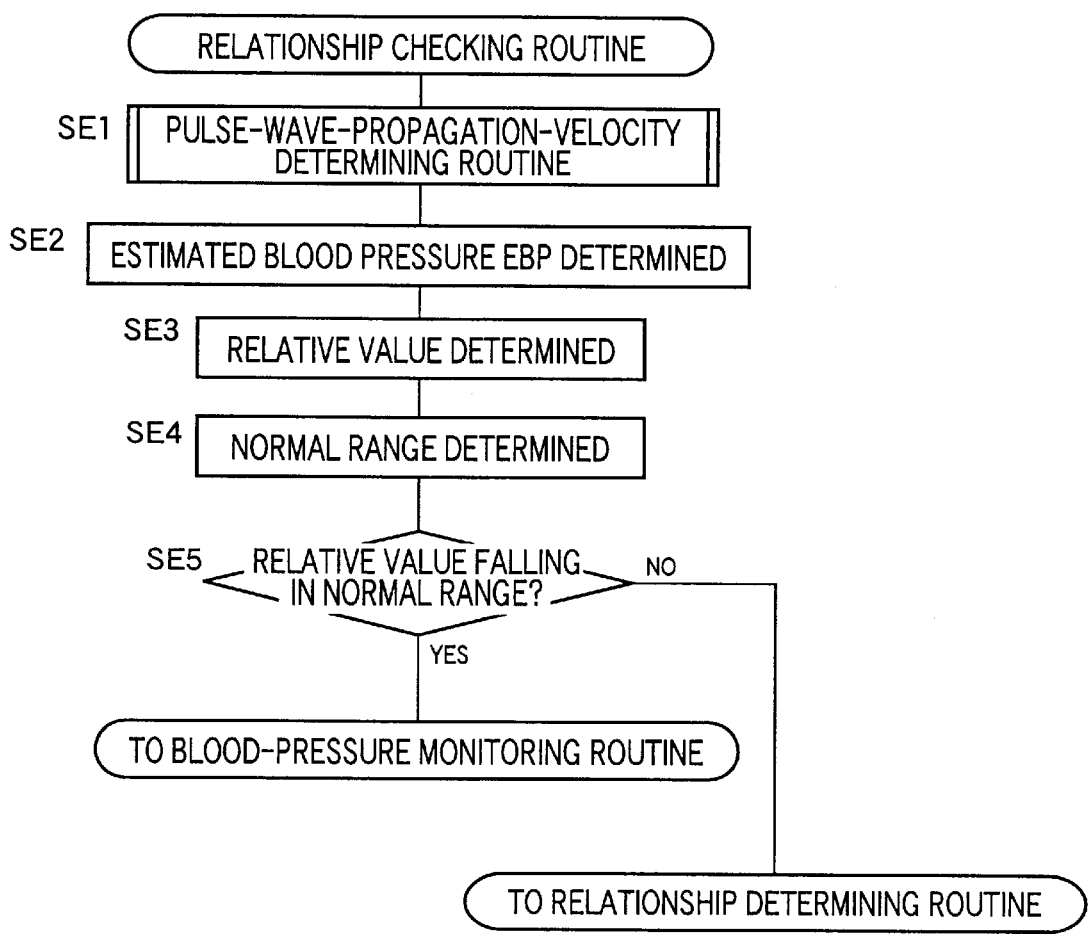
FIG. 17 is a flow chart representing a relationship checking routine according to which the control device shown in FIG. 16 judges whether a relationship between blood pressure and pressure pulse wave is appropriate.

FIG. 17 is a flow chart representing essential functions of the control device 48 shown in FIG. 16. More specifically described, FIG. 17 shows a relationship checking routine for judging whether the relationship between blood pressure and pressure pulse wave is appropriate. In addition, the control device 48 is operated according to the relationship determining routine of FIG. 12, the pulse-wave-propagation-velocity determining routine of FIG. 13, and the blood-pressure monitoring routine of FIG. 14.

In FIG. 17, first, at SE1, the control device 48 carries out the pulse-wave-propagation-velocity determining routine of FIG. 13, and determines a judgment pulse-wave-propagation velocity PWV2. Then, at SE2 corresponding to the estimated-blood-pressure determining means 162, the control device 48 determines, according to the expression (3) determined or updated at SA12 of the relationship determining routine (FIG. 12), an estimated diastolic blood pressure $EBP_{DIA}$ of the patient based on the judgment pulse-wave propagation velocity PWV2 determined at SE1.

Subsequently, at SE3, the control device 48 determines a ratio of the monitor diastolic blood-pressure value $MBP_{DIA}$ determined at SC2 of the blood-pressure monitoring routine (FIG. 14) to the estimated diastolic blood-pressure value $EBP_{DIA}$ determined at SE2, as a relative value of the value $MBP_{DIA}$ to the value $EBP_{DIA}$.

Next, at SE4 corresponding to the normal-range determining means 174, the control device 48 judges whether at least one of the estimated diastolic blood-pressure value $EBP_{DIA}$ determined at SE2 and the monitor diastolic blood-pressure value $MBP_{DIA}$ determined at SC2 of FIG. 14 is lower than the prescribed danger value, i.e., 70 mmHg. If a positive judgment is made, the control device 48 determines, as the normal range to be used at SE5 to check the relationship between blood pressure and pressure pulse wave, a narrower normal range than the standard normal range determined if a negative judgment is made. In the case where the standard normal range ranges from 0.8 to 1.2, the narrower range may range from 0.85 to 1.15.

Subsequently, the control goes to SE5 corresponding to the relationship checking means 172. At SE5, the control device 48 judges whether the relative value determined at SE3 falls within the normal range determined at SE4. If a positive judgment is made at SE5, the control goes to the blood-pressure monitoring routine of FIG. 14. On the other hand, a negative judgment made at SE5 indicates that the relationship between blood pressure and pressure pulse wave is not appropriate and accordingly the accuracy of the monitor blood-pressure value MBP is not sufficient. Hence, the control goes to the relationship determining routine of FIG. 12, so that the second pressure-pulse-wave sensor 32 is pressed again appropriately and the relationship between blood pressure and pressure pulse wave is updated.

In the illustrated embodiment in which the above-described flow chart is employed, at SE2 (the estimated-blood-pressure determining means 162), the control device 48 determines the estimated blood-pressure value EBP based on the judgment pulse-wave propagation velocity PWV2 according to the relationship between blood pressure and pulse-wave-propagation-velocity-related information. If the condition under which the second pressure-pulse-wave sensor 32 is worn on the patient has changed and accordingly the monitor blood-pressure value MBP determined at SC2 (the blood-pressure monitoring means 142) is not accurate, the monitor blood-pressure value MBP largely differs from the estimated blood-pressure value EBP. Hence, at SE5 (the relationship checking means 174), the control device 48 compares the estimated blood-pressure value EBP and the monitor blood-pressure value MBP determined at SC2 (the blood-pressure monitoring means 142), with each other, and judges whether the relationship between blood pressure and pressure pulse wave, determined at SA10 (the first relationship determining means 140) is appropriate or not.

Therefore, a longer calibration period Tc can be employed to carry out SA7 (the blood-pressure determining means 138) and thereby update the relationship between blood pressure and pressure pulse wave, and accordingly the discomfort the patient feels can be reduced. Moreover, since the pulse-wave propagation velocity PWV can each be determined based on only the signal obtained by the first pressure-pulse-wave sensor 68, the pressure-pulse-wave detecting probe 12 can be worn on the other arm than the arm around which the cuff 52 is wound.

While the present invention has been described in its preferred embodiments by reference to the drawings, it is to be understood that the invention may otherwise be embodied.

For example, the illustrated continuous blood-pressure monitoring apparatus 10 employs the two kinds of pressure-pulse-wave sensors, i.e., the first pressure-pulse-wave sensors 68 and the second pressure-pulse-wave sensor 32. However, as described previously, the apparatus may employ only one of the two sorts of pressure-pulse-wave sensors, and determine the monitor blood pressure MBP and obtains the pulse-wave-propagation-velocity-related information based on the pressure pulse wave detected by the one sort of sensor.

In addition, in the illustrated continuous blood-pressure monitoring apparatus 10, the first pressure-pulse-wave sensors 68 are provided on the inner surface of the cuff 52 such that the first sensors 68 are integral with the large cuff 58 used to measure the blood pressure of the patient. However, the the first pressure-pulse-wave sensors or sensor 68 may be provided independent of the large cuff 58. In the latter case, the first pressure-pulse-wave sensors or sensor 68 may be worn on an upper arm or wrist of the other arm than the arm on which the large cuff 58 is worn.

Each of the first pressure-pulse-wave sensors 68 includes the pressure-sensing semiconductor elements 72 to detect respective pressure pulse waves. However, it is possible to employ a different type of pressure sensor, e.g., a diaphragm-type pressure sensor that utilizes the change of resistance of a strain gauge, formed in a diaphragm, when the gauge is displaced by a pressure exerted thereto. In addition, the cuff-pulse-wave signal SW extracted by the high-pass filter 82 and the low-pass filter 88 from the first pressure signal SP1 provided by the pressure sensor 74, also represents a brachial-artery pressure pulse wave BAP produced from the brachial artery 146. Therefore, the pressure sensor 74, the high-pass filter 82, and the low-pass filter 88 may be used as a first pressure-pulse-wave sensor.

While the present invention has been described in detail in its preferred embodiments by reference to the drawings, it is to be understood that the present invention is not limited to those details of the described embodiments and may be embodied with other changes and improvements that may occur to a person skilled in the art without departing from the spirit and scope of the invention defined in the appended claims.

What is claimed is:

1. An apparatus for continuously monitoring a blood pressure of a living subject, comprising:

an inflatable cuff which is adapted to be wound around a portion of the subject;

a blood-pressure determining means for determining a blood pressure of the subject based on a signal obtained while a pressure in the cuff is changed;

a relationship determining means for determining a relationship between blood pressure and magnitude of pressure pulse wave, based on the blood pressure determined by the blood-pressure determining means and a magnitude of a first-artery pressure pulse wave detected from a first artery of the subject;

a blood-pressure monitoring means for iteratively determining, according to the thus determined relationship, a monitor blood-pressure value of the subject based on a magnitude of each of a plurality of heartbeat-synchronous pulses of the first-artery pressure pulse wave detected from the first artery;

a first pressure-pulse-wave sensor which is adapted to be worn on a portion of the subject that is distant from a chest of the subject, detects a second-artery pressure pulse wave that is produced by a second artery of said portion, and produces a pressure-pulse-wave signal representing the detected second-artery pressure pulse wave;

a heart-sound extracting means for extracting, from the pressure-pulse-wave signal produced by the pressure-pulse-wave sensor, a heart-sound component representing heart sounds generated by a heart of the subject;

a pulse-wave-propagation-velocity-related-information obtaining means for iteratively obtaining a piece of pulse-wave-propagation-velocity-related information which is related to a velocity at which the second-artery pressure pulse wave propagates through the second artery of the subject, based on a time of occurrence of a prescribed periodic point of a heartbeat-synchronous pulse of the heart-sound component extracted by the heart-sound extracting means and a time of occurrence of a prescribed periodic point of a corresponding heartbeat-synchronous pulse of the second-artery pressure pulse wave detected by the pressure-pulse-wave sensor;

a propagation-velocity-related-information-change-value determining means for periodically determining, at a prescribed judgment period, a change value of the pieces of pulse-wave-propagation-velocity-related information obtained by the pulse-wave-propagation-velocity-related-information obtaining means;

a monitor-blood-pressure-change-value determining means for periodically determining, at the judgment period, a change value of the monitor blood-pressure values determined by the blood-pressure monitoring means; and a relationship checking means for comparing the change value of the pieces of pulse-wave-propagation-velocity-related information, determined by the propagation-velocity-related-information-change-value determining means, and the change value of the monitor blood-pressure values, determined by the monitor-blood-pressure-change-value determining means, with each other, and thereby judging whether the relationship between blood pressure and magnitude of pressure pulse wave, determined by the relationship determining means, is appropriate.

2. An apparatus according to claim 1, further comprising a second pressure-pulse-wave sensor which is adapted to be pressed against the first artery of the subject and detects the first-artery pressure pulse wave generated by the first artery, wherein the first pressure-pulse-wave sensor is adapted to be worn on said portion of the subject that is more proximal to the heart of the subject than the first artery against which the second pressure-pulse-wave sensor is adapted to be pressed.

3. An apparatus according to claim 1, wherein the relationship checking means judges that the relationship between blood pressure and magnitude of pressure pulse wave is not appropriate, when a relative value between the change value of the pieces of pulse-wave-propagation-velocity-related information, determined by the propagation-velocity-related-information-change-value determining means, and the change value of the monitor blood-pressure values, determined by the monitor-blood-pressure-change-value determining means, does not fall within a normal range.

4. An apparatus according to claim 3, further comprising a normal-range determining means for determining, as the normal range, a narrower range when the monitor blood-pressure value used to determine the change value of the monitor blood-pressure values is lower than a prescribed danger value which indicates that the subject needs an urgent treatment, than a range determined thereby when the monitor blood-pressure value is not lower than the danger value.

5. An apparatus according to claim 1, wherein the relationship checking means comprises means for operating, when it is judged that the relationship between blood pressure and magnitude of pressure pulse wave is not appropriate, the relationship determining means to update said relationship.

6. An apparatus according to claim 1, further comprising:
a pressure changing device which changes the pressure of the cuff, and
a pressure sensor which detects the pressure of the cuff changed by the pressure changing device.

7. An apparatus for continuously monitoring a blood pressure of a living subject, comprising:
an inflatable cuff which is adapted to be wound around a portion of the subject;
a blood-pressure determining means for determining a blood pressure of the subject based on a signal obtained while a pressure in the cuff is changed;
a first relationship determining means for determining a relationship between blood pressure and magnitude of pressure pulse wave, based on the blood pressure determined by the blood-pressure determining means and a magnitude of a first-artery pressure pulse wave detected from a first artery of the subject;

a blood-pressure monitoring means for iteratively determining, according to the thus determined relationship, a monitor blood-pressure value of the subject based on a magnitude of each of a plurality of heartbeat-synchronous pulses of the first-artery pressure pulse wave detected from the first artery;

a first pressure-pulse-wave sensor which is adapted to be worn on a portion of the subject that is distant from a chest of the subject, detects a second-artery pressure pulse wave that is produced by a second artery of said portion, and produces a pressure-pulse-wave signal representing the detected second-artery pressure pulse wave;

a heart-sound extracting means for extracting, from the pressure-pulse-wave signal produced by the pressure-pulse-wave sensor, a heart-sound component representing heart sounds generated by a heart of the subject;

a standard-pulse-wave-propagation-velocity-related-information obtaining means for obtaining, as a standard piece of pulse-wave-propagation-velocity-related information, a piece of pulse-wave-propagation-velocity-related information which is related to a velocity at which the second-artery pressure pulse wave propagates through the second artery of the subject, based on a time of occurrence of a prescribed periodic point of a heartbeat-synchronous pulse of the heart-sound component in a first time duration comprising at least one of a first time period in which the pressure of the cuff is changed, a prescribed preceding time period preceding the first time period, and a prescribed following time period following the first time period, and a time of occurrence of a prescribed periodic point of a corresponding heartbeat-synchronous pulse of the second-artery pressure pulse wave in the first time duration;

a second relationship determining means for determining a second relationship between blood pressure and pulse-wave-propagation-velocity-related information, based on the blood pressure determined by the blood-pressure determining means and the standard piece of pulse-wave-propagation-velocity-related information obtained by the standard-pulse-wave-propagation-velocity-related-information obtaining means;

a judgment-pulse-wave-propagation-velocity-related-information obtaining means for obtaining, as a judgment piece of pulse-wave-propagation-velocity-related information, a piece of pulse-wave-propagation-velocity-related information which is related to the velocity at which the second-artery pulse wave propagates through the second artery of the subject, based on a time of occurrence of a prescribed periodic point of a heartbeat-synchronous pulse of the heart-sound component extracted by the heart-sound extracting means, and a time of occurrence of a prescribed periodic point of a corresponding heartbeat-synchronous pulse of the second-artery pressure pulse wave detected by the pressure-pulse-wave sensor, at a prescribed judgment period;

an estimated-blood-pressure determining means for determining, according to the second relationship, an estimated blood-pressure value of the subject based on the judgment piece of pulse-wave-propagation-velocity-related information obtained by the judgment-pulse-wave-propagation-velocity-related-information obtaining means; and a relationship checking means for comparing, at the judgment period, the estimated blood-pressure value determined by the estimated-blood-pressure determining means, and a monitor blood-pressure value determined by the blood-pressure monitoring means based on a magnitude of a heartbeat-synchronous pulse of the first-artery pressure pulse wave detected at a time around a time when the judgment piece of pulse-wave-propagation-velocity-related information is obtained by the judgment-pulse-wave-propagation-velocity-related-information obtaining means, with each other, and thereby judging whether the relationship between blood pressure and magnitude of pressure pulse wave, determined by the first relationship determining means, is appropriate.

8. An apparatus according to claim 7, further comprising a second pressure-pulse-wave sensor which is adapted to be pressed against the first artery of the subject and detects the first-artery pressure pulse wave generated by the first artery, where the first pressure-pulse-wave sensor is adapted to be worn on said portion of the subject that is more proximal to the heart of the subject than the first artery against which the second pressure-pulse-wave sensor is adapted to be pressed.

9. An apparatus according to claim 7, wherein the relationship checking means judges that the relationship between blood pressure and magnitude of pressure pulse wave is not appropriate, when a relative value between the estimated blood-pressure value determined by the estimated-blood-pressure determining means, and the monitor blood-pressure value determined by the blood-pressure monitoring means does not fall within a normal range.

10. An apparatus according to claim 9, further comprising a normal-range determining means for determining, as the normal range, a narrower range when at least one of the estimated blood-pressure value and the monitor blood-pressure value is lower than a prescribed danger value which indicates that the subject needs an urgent treatment, than a range determined thereby when each of the estimated blood-pressure value and the monitor blood-pressure value is not lower than the danger value.

11. An apparatus according to claim 7, wherein the relationship checking means comprises means for operating, when it is judged that the first relationship between blood pressure and magnitude of pressure pulse wave is not appropriate, the first relationship determining means to update the first relationship.

* * * * *